United States Patent
Norquist et al.

(10) Patent No.: US 6,767,492 B2
(45) Date of Patent: Jul. 27, 2004

(54) EXTRUSION DIE AND PROCESS

(75) Inventors: Scott G Norquist, St. Paul, MN (US); Dennis L Krueger, Hudson, WI (US); Alan J. Sipinen, North Oaks, MN (US); Thomas P Hanschen, St. Paul, MN (US); Ronald P Leseman, Newport, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 212 days.

(21) Appl. No.: 10/185,218

(22) Filed: Jun. 27, 2002

(65) Prior Publication Data

US 2002/0195738 A1 Dec. 26, 2002

Related U.S. Application Data

(62) Division of application No. 09/365,286, filed on Jul. 30, 1999, now Pat. No. 6,447,875.

(51) Int. Cl.[7] ............................................. B29C 47/06
(52) U.S. Cl. ............................ 264/173.15; 264/210.1; 425/131.1; 425/380; 425/467
(58) Field of Search ...................... 264/173.15, 173.12, 264/173.16, 210.1; 425/131.1, 380, 467

(56) References Cited

U.S. PATENT DOCUMENTS

| | | | |
|---|---|---|---|
| 3,485,912 A | | 12/1969 | Schrenk et al. |
| 3,565,737 A | | 2/1971 | Lefevre et al. |
| 3,792,945 A | | 2/1974 | Randall |
| 3,807,918 A | * | 4/1974 | Chill et al. ............... 425/133.5 |
| 3,884,606 A | * | 5/1975 | Schrenk ................... 425/133.5 |
| 4,165,210 A | * | 8/1979 | Corbett .................... 425/133.5 |
| 4,197,069 A | | 4/1980 | Cloeren |
| 4,316,868 A | | 2/1982 | Esposito et al. |
| 4,435,141 A | | 3/1984 | Weisner et al. |

(List continued on next page.)

FOREIGN PATENT DOCUMENTS

| | | |
|---|---|---|
| DE | 19806452 A | 8/1999 |
| EP | 0641639 A1 | 3/1995 |
| JP | 6-293067 | 10/1994 |

OTHER PUBLICATIONS

Bird, R., et al., *Dynamics of Polymeric Liquids*, vol. 1, Fluid Mechanics, 2d ed., John Wiley & Sons, N.Y., 1987, p. 176.

*Primary Examiner*—Mark Eashoo
(74) *Attorney, Agent, or Firm*—Douglas B. Little

(57) ABSTRACT

A die apparatus, a method of using the die apparatus to produce co-extruded polymeric articles, and co-extruded polymeric articles produced using the die apparatus and method are disclosed. The die apparatus includes a hollow vane configured to extrude a material into a chamber within the die, thereby producing a co-extruded web. The co-extruded web has a plurality of distinct, discontinuous phases in the cross-web direction, the phases having a uniform width as shown by a coefficient of variation of less than 8 percent for any three consecutive phases. The phases are substantially continuous down-web and are surrounded by a matrix having two or more layers.

5 Claims, 8 Drawing Sheets

U.S. PATENT DOCUMENTS

| | | |
|---|---|---|
| 4,464,157 A | 8/1984 | Benoit et al. |
| 4,469,782 A * | 9/1984 | Ishiwata et al. ............ 430/502 |
| 4,521,359 A | 6/1985 | Tsien |
| 4,533,308 A | 8/1985 | Cloeren |
| 4,536,362 A | 8/1985 | Donaldson |
| 4,592,938 A | 6/1986 | Benoit |
| 4,731,004 A | 3/1988 | Wenz, Jr. |
| 4,784,815 A | 11/1988 | Cloeren et al. |
| 4,787,897 A | 11/1988 | Torimae et al. |
| 4,923,551 A | 5/1990 | Wagers et al. |
| 5,110,530 A * | 5/1992 | Havens ................. 264/173.15 |
| 5,145,544 A | 9/1992 | Leseman et al. |
| 5,173,141 A | 12/1992 | Leseman et al. |
| 5,217,794 A | 6/1993 | Schrenk |
| 5,298,310 A | 3/1994 | Havens |
| 5,316,703 A | 5/1994 | Schrenk |
| 5,462,708 A | 10/1995 | Swenson et al. |
| 5,464,107 A | 11/1995 | Koeniger |
| 5,468,428 A | 11/1995 | Hanschen et al. |
| 5,589,122 A | 12/1996 | Leonard et al. |
| 5,660,922 A | 8/1997 | Herridge et al. |
| 5,750,159 A | 5/1998 | Delmore |
| 5,773,374 A | 6/1998 | Wood et al. |
| 5,792,529 A | 8/1998 | May |
| 5,800,903 A | 9/1998 | Wood et al. |
| 6,221,483 B1 | 4/2001 | Hilston et al. |
| 6,270,910 B1 | 8/2001 | Jaeger et al. |
| 6,447,875 B1 * | 9/2002 | Norquist et al. ............ 428/107 |
| 6,669,887 B2 * | 12/2003 | Hilston et al. ......... 264/173.15 |

* cited by examiner

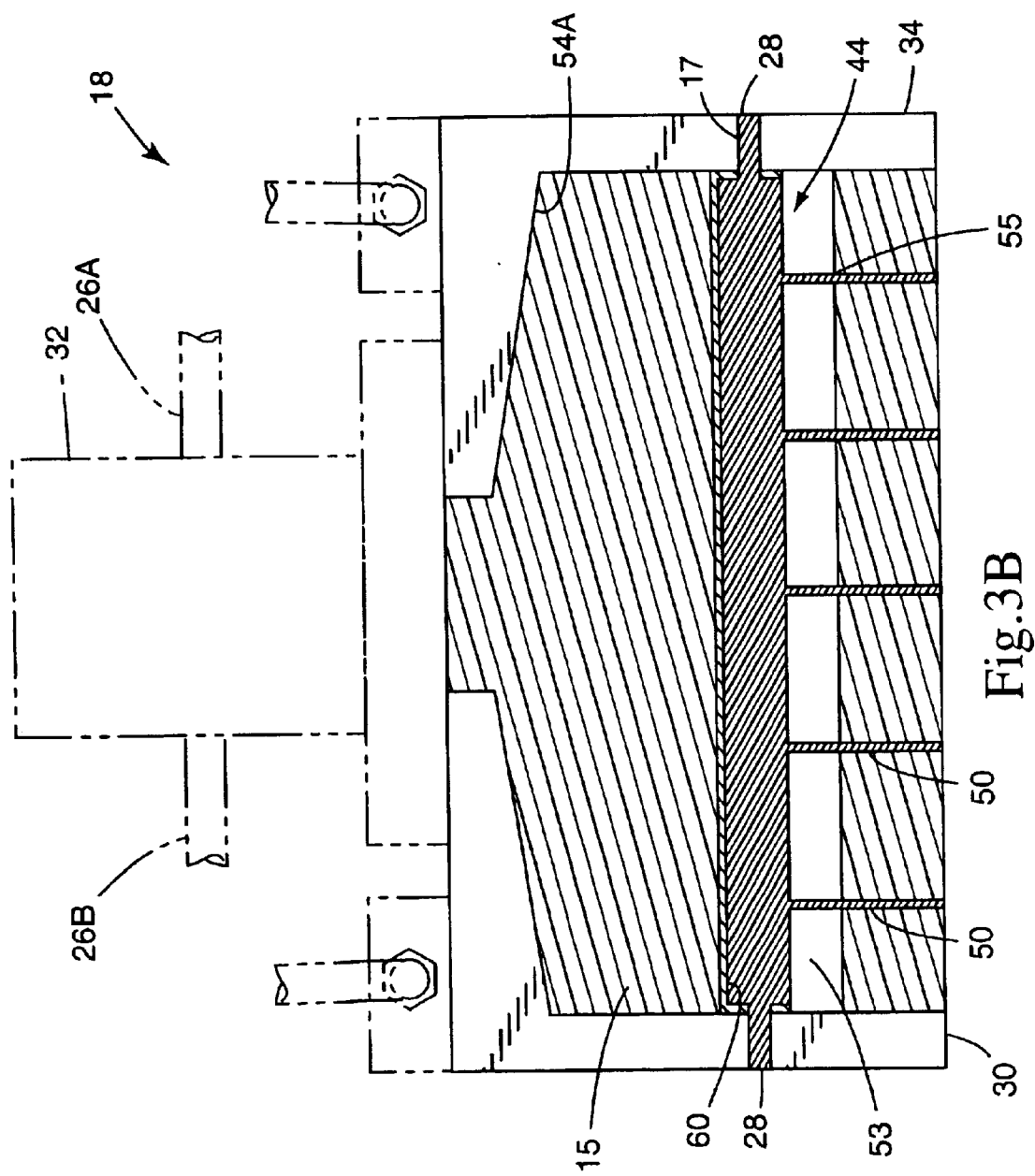

EXTRUSION DIE AND PROCESS

CROSS REFERENCE TO RELATED APPLICATIONS

This application is a divisional of U.S. Application No. 09/365,286, filed Jul. 30, 1999 now U.S. Pat. No. 6,447,875.

FIELD OF THE INVENTION

The present invention is directed to an extrusion die, a method of using the die to produce co-extruded polymeric articles, and co-extruded polymeric articles produced therewith having internal discontinuities, such as stripes.

BACKGROUND OF THE INVENTION

Extruded polymeric webs are used in many applications, including the production of thin films for use as tape backings, medical films, and vapor barriers. Polymeric materials that are suitable for extrusion are often polyolefins such as polyethylene, polypropylene, and polybutylene; polyamides such as nylon; polyesters such as polyethylene terephthalate; or polyvinylidene fluoride. Although these polymeric materials and others are suitable for use in forming a polymeric web, they can have limiting characteristics that substantially narrow their suitable uses. For example, reinforced polypropylene webs often have very good tensile strength, but have less than desirable cross-web tear strength. Therefore, due to a propensity to tear too easily in the cross-web direction, oriented polypropylene webs do not traditionally make satisfactory products requiring cross-web strength, such as strapping tape products. Similarly, natural and synthetic rubber have excellent elasticity, but are difficult to fuse with most polymeric materials. Therefore, due to the challenge of creating a good bond between materials, rubber webs are difficult to use in products that require them to be joined with other polymeric materials.

A hybrid polymeric web combining two polymers is described in Krueger et al. (U.S. Pat. No. 5,429,856). An apparatus for making a co-extruded web is disclosed in Schrenk et al. (U.S. Pat. No. 3,485,912).

DISCLOSURE OF INVENTION

In certain embodiments of the invention, the polymeric co-extruded web comprises a plurality of uniform, distinct, phases (embedded phases) that are discontinuous in a cross-web direction. The embedded phases preferably have a width uniform to within a coefficient of variation of less than 8 percent for three consecutive discontinuous phases. The width of these embedded phases is measured in a cross-section of the co-extruded web cut transverse (i.e., cross-web) to the machine direction (i.e., down-web) and is the largest dimension of the cross-section of the embedded phases in the cross-web direction. The embedded phases are substantially continuous down-web and are surrounded by a matrix having two or more distinct layers of the same or different materials.

In one embodiment, the discontinuous phases of the polymeric co-extruded web are spaced at substantially uniform intervals in the cross-web direction. In another embodiment, the plurality of discontinuous phases consists of a first discontinuous phase positioned proximate a first edge of the web, and a second discontinuous phase positioned proximate a second edge of the web.

The present invention is also directed to an extrusion die for forming a polymeric co-extruded web. In specific embodiments, the die includes a body containing two chambers. An adjustable vane is positioned between the chambers. The adjustable vane is at least partially hollow, having a cavity within its interior. The vane has at least one opening (inlet) in the cavity positioned to receive a material being extruded, and at least two openings (outlets) in the cavity positioned in a tip to extrude material into the body of the die. The cavity inlets and outlets are sized so that the width of the embedded phases extruded from the vane outlets into the die body are uniform. This uniformity of the embedded phases is an advantage of this invention.

In operation, a first material is forced into the chambers of the body of the die, and a second material is forced into the cavity of the vane. The first material is conveyed through the chambers of the die, passing around and past the vane. The second material enters the cavity of the vane and subsequently flows out through the tip of the vane oriented toward the downstream end of the die and into the die body, where it flows along with the first material in laminar flow until the combined materials exit the die to form a co-extruded web.

The invention is further directed to a process of making a polymeric co-extruded web. The process includes providing an extrudable material and an extrusion die. In a specific embodiment, the die contains two chambers and an adjustable vane between the chambers. The vane contains a cavity having at least one input orifice positioned to receive extrudable material and at least two exit orifices. The cavity is designed so that the pressure drop of molten polymer within the cavity is significantly less than the pressure drop through the exit orifices to yield embedded phases of improved width uniformity over those extruded by known techniques. A first material is extruded through the chambers of the die, and a second material is extruded through the exit orifice in the vane to produce a co-extruded web containing the first and second extrudable materials. The second material is embedded between the two layers of the first material. Alternatively, different polymeric materials may pass through each die chamber to form two layers of different materials that are positioned around the embedded phase material.

BRIEF DESCRIPTION OF THE DRAWINGS

FIG. 3B is a cross-sectional view of the extrusion die shown in FIG. 2A, taken along section line 3B of FIG. 3A.

DETAILED DESCRIPTION OF THE INVENTION

Figure 1:
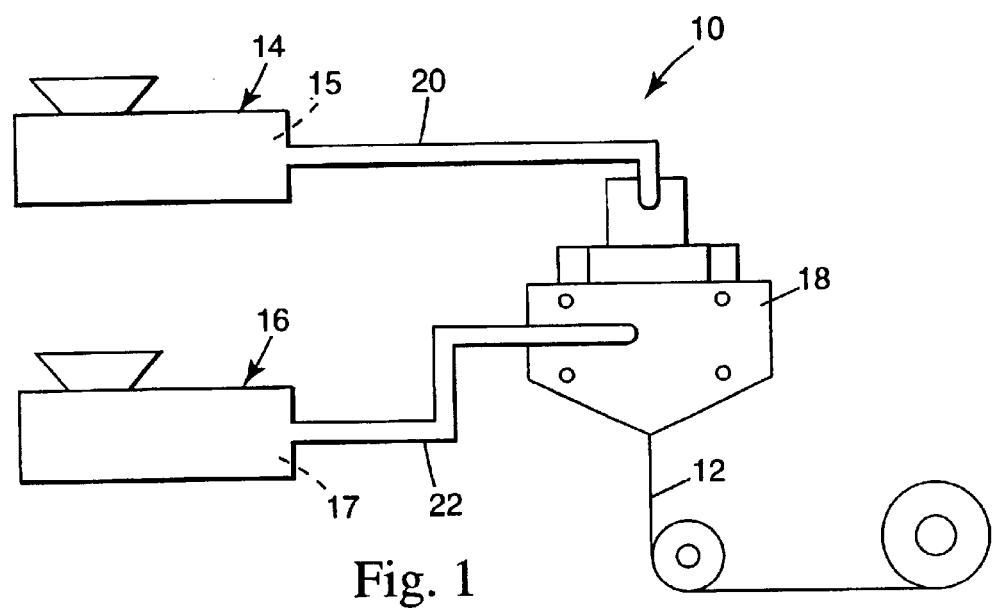
FIG. 1 is a schematic view of a system for production of a co-extruded web in accordance with an embodiment of the invention.

FIG. 1 shows a schematic view of an extrusion system 10 for manufacturing a co-extruded polymeric web 12 in accordance with an embodiment of the invention. In the embodiment depicted, system 10 includes extruders 14 and 16, as well as an extrusion die 18. The extruders 14 and 16 respectively contain first and second extrudable materials 15 and 17 and provide molten streams of first and second extrudable materials 15 and 17 along conduits 20 and 22 to extrusion die 18. As detailed below, the extrudable materials 15 and 17 are extruded from the die 18 such that first extrudable material 15 substantially surrounds or forms a matrix around second extrudable material 17, which becomes the discontinuous phases embedded within the matrix having two layers. Alternatively, a third extruder may be used to feed a third material into the die 18 to form a matrix having a different material for each matrix layer.

Figure 4:
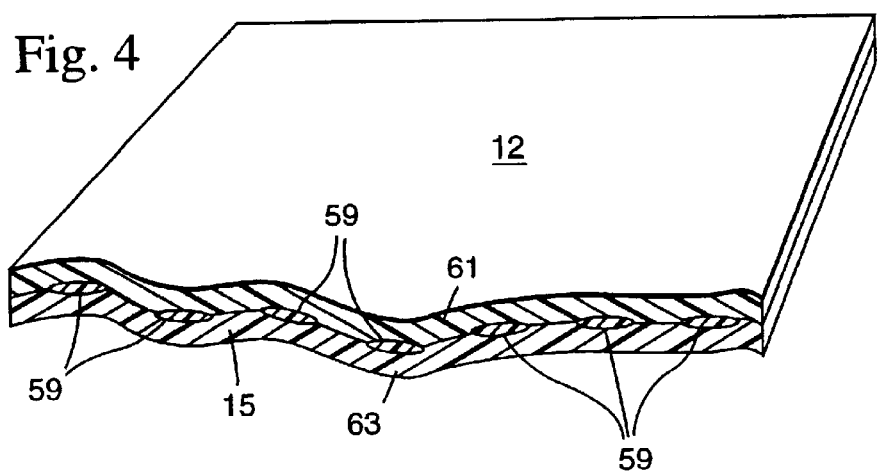
FIG. 4 is a perspective view of a polymeric web made in accordance with the invention and showing the web in cross-section.
Figure 2A:
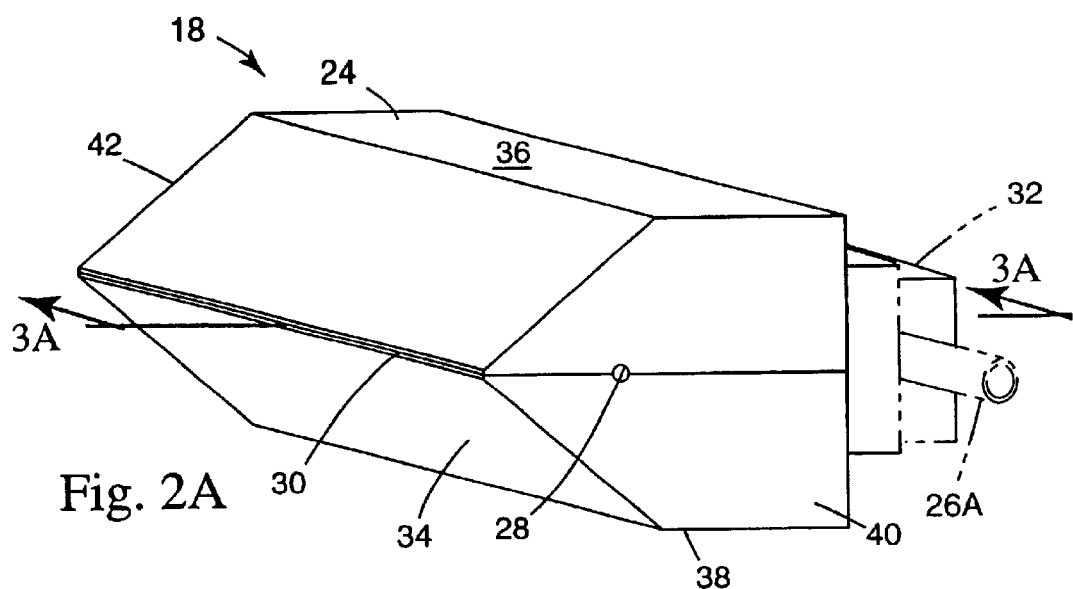
FIG. 2A is a perspective view of an extrusion die constructed in accordance with an embodiment of the invention.

The manner in which the co-extruded web 12 is formed is shown in more particularity in FIGS. 2A through 3B. In addition, FIG. 4 shows an embodiment of the co-extruded web 12 produced by use of system 10. With reference now to FIG. 2A, a perspective view of the extrusion die 18 is depicted showing a body 24 that has at least first and second orifices 26 and 28. Orifice 26 provides entry for the first extrudable material 15 from conduit 20, while orifice 28 provides entry for the second extrudable material 17 from conduit 22. Optionally, the first material could be passed thorough orifice 26A and the third material could be passed through orifice 26B. In addition, a second embedded phase material could be introduced through orifices 28 on the sides of die 18. However, in that case, a separating means (e.g., partition) within vane 44 preferably would be added to prevent mixing of the two embedded phase materials within vane 44. Extrusion die 18 also includes an exit port 30. The width of port 30 (also called the die gap) is typically 1000 µm or less, for elastic webs typically 100–250 µm.

The extrudable materials 15 and 17 enter extrusion die 18 at orifices 26 and 28, respectively, flow through die 18, and then leave die 18 at exit port 30 as co-extruded web 12. Therefore, die 18 has a generally upstream end 32 and a generally down stream end 34. In addition, in the embodiment represented, die 18 includes a top 36, an opposite bottom 38, a first side 40 and an opposite second side 42.

Figure 2B:
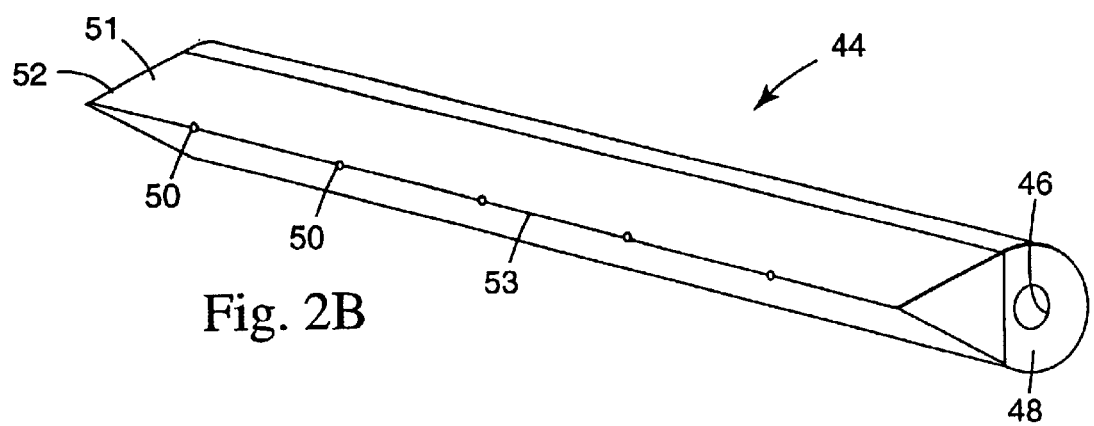
FIG. 2B is a perspective view of an extrusion die vane constructed in accordance with an embodiment of the invention.

Within extrusion die 18 is an adjustable vane 44, shown in FIG. 2B. Adjustable vane 44 includes at least two types of orifices 46 and 50. Entrance orifice or orifices 46 allow entry of polymeric material 17 into the interior of vane 44, and outlet orifice 50 permit the exit of polymeric material 17 from the interior of vane 44. In the embodiment depicted, entrance orifices 46 (one not shown) are positioned along a side of back section 48 of vane 44. Also in the embodiment depicted, a plurality of outlet orifices 50 are positioned along front 51 of vane 44 at downstream end 52 of vane 44. The outlet orifices can be made by EDM (electro-discharge machining) or other material removal means known in the art. The shape and position of orifices 50 define the shape and position of the plurality of distinct embedded phases in the polymeric web. Advantageously, tip 53 of vane 44 may be removable and replaceable to allow placement of different tips having different configurations of orifices 50 to form different web configurations.

Vane 44 is thus adjustable in as least one of two modes. The vane can be pivoted so the tip can be moved closer to the exit of one die chamber or the other causing a difference in die gap for the exits of each of the two matrix layers. This can result in a different matrix layer thickness if each layer is made with matrix material having a similar melt viscosity. Alternatively, different exit gaps can result in a similar matrix layer thickness if each layer is made with matrix material having a different melt viscosity. The vane can also be adjusted by replacement of tip 53 with one having orifices of different shapes and spacing.

Figure 3A:
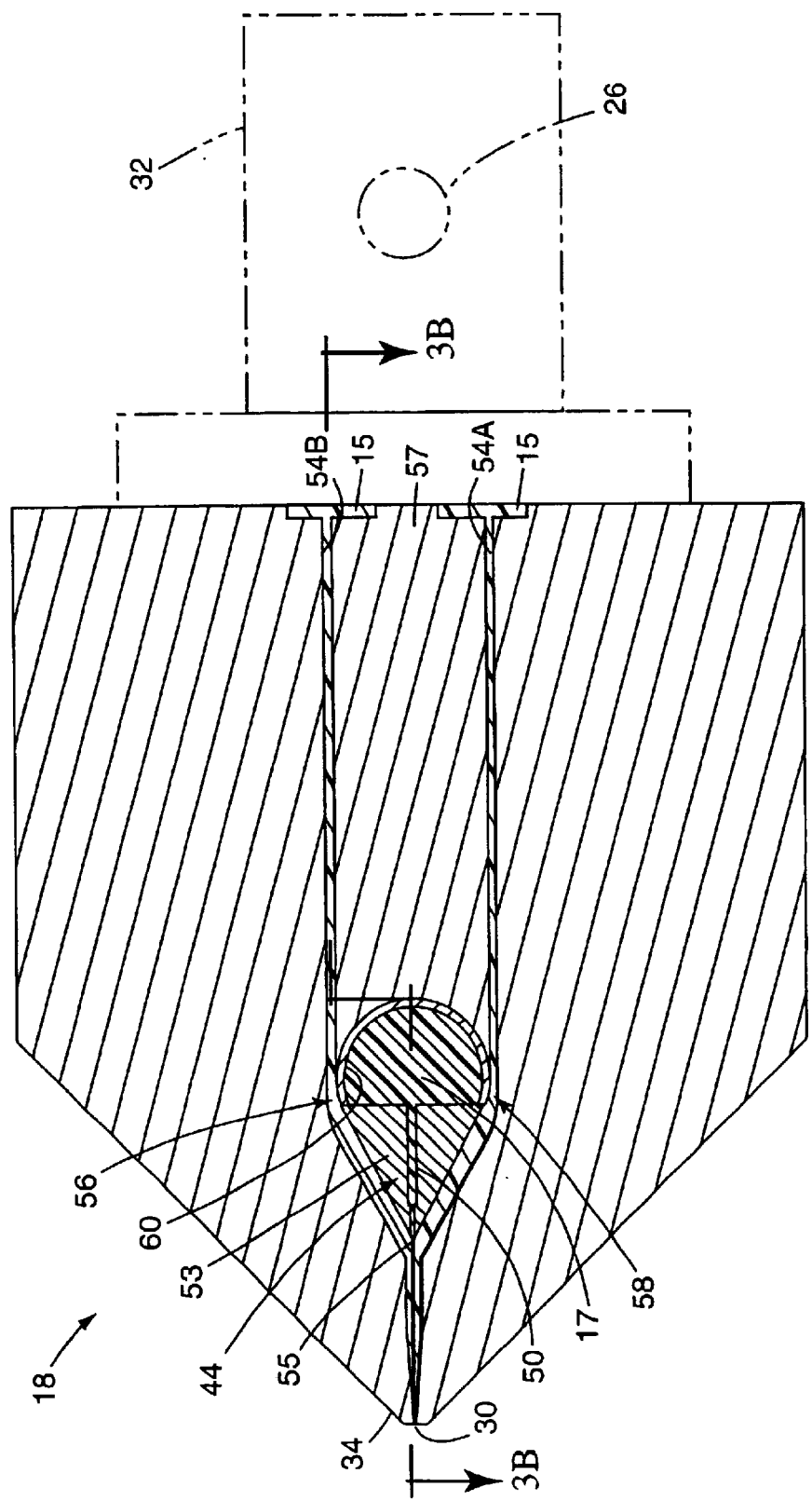
FIG. 3A is a cross-sectional view of the extrusion die shown in FIG. 2A, taken along plane 3A of FIG. 2A.

The interior construction of vane 44, and the position of vane 44 within die 18, are more completely shown in FIGS. 3A and 3B, which are cross-sections of die 18. FIGS. 3A and 3B also show more clearly the manner in which the extrudable materials 15 and 17 are combined to make the co-extruded polymeric web 12. Extrusion die 18 includes internal chambers 54A and 54B that are in part separated by vane 44. An internal divider 57 is positioned and fastened within the die 18, and defines the extent of a portion of each of the chambers 54A and 54B. Chambers 54A and 54B typically have a combined volume greater than vane 44, and thus upper gap 56 is formed above vane 44 and lower gap 58 is formed below vane 44. Vane 44 is arranged such that it can move within chambers 54A and 54B. In certain embodiments, vane 44 can be rotated about an axis corresponding to the orifice 46 (shown in FIG. 2B).

Vane 44 contains a cavity 60 that is connected to the orifice 46. Cavity 60 receives material 17, which is subsequently forced under pressure through the plurality of exit orifices 50 (of which one is depicted in cross section in FIG. 3A).

The sizes of the cross section of cavity 60 normal to the direction of embedded phase material flowing into the cavity and the size and number of exit orifices 50 are made to have sufficient pressure drop through exit orifices 50 to yield the good width uniformity in the embedded phases described above. These parameters are determined using the flow rate equation for a power-law fluid as described in Bird, R., et al., *Dynamics of Polymeric Liquids*, Volume 1, Fluid Mechanics, 2d ed., John Wiley & Sons, N.Y., 1987, p. 176

$$Q = \frac{\pi R^3}{(1/n)+3}\left(\frac{(P_o - P_L)R}{2\,mL}\right)^{1/n}$$

in which

Q=volumetric flow rate, and is assumed equal for all exit orifices of the same size.
R=orifice radius
$P_O$=Pressure at beginning of tube or orifice
$P_L$=Pressure at end of tube or orifice
$P_O - P_L = \Delta P$
L=tube or orifice length
m and n are Power Law constants. For purposes of this description, n is normally in the range of 0.2–0.8 and m is normally in the range of 3,000 to 20,000. The calculation below uses m=11100 and n=0.28 which are good approximations for standard extrusion grade polypropylene.

Using this equation, the pressure drop of the flowing embedded phase polymer can be calculated:

$$\Delta P = \left(\frac{Q((1/n)+3)}{\pi R^3}\right)^n \left(\frac{2\,mL}{R}\right)$$

For example, given: Q total polymer flow of 15 lb/hr, a polymer density of 1 g./cm³, 95 exit orifices 50, R=1.9×10⁻⁴ m and L=5.13×10⁻³ m $$Q_T = 15\frac{lb}{hr} = 1.89 \times 10^{-6}\frac{m^3}{sec}$$

$$Q = \frac{Q_T}{95} = 1.99 \times 10^{-8}\frac{m^3}{sec}$$

$$\Delta P_{orifice} = \left(\frac{\left(1.99 \times 10^{-8}\frac{m^3}{sec}\right)\left(\frac{1}{0.28}+3\right)}{\pi(1.9 \times 10^{-4})^3}\right)^{0.28} \left(\frac{2(11,100) \times 5.13 \times 10^{-3}}{1.9 \times 10^{-4}}\right)$$

= 6.87 MPa or 997 psi is the pressure drop through the exit orifices.

Using the same equation and solving for ΔP through a cavity of length 0.4572 m (18 in.), inside radius of 0.0095 m:

$\Delta P_{cavity}$=1.64 MPa or 238 psi

The ratio of pressure drop through the exit orifices to pressure drop through the cavity is about 4.

Using this type of calculation the ratio of $\Delta P_{orifice}:\Delta P_{cavity}$ is preferably at least 1.5.

In addition, the exit orifices should be spaced apart from each other enough so that the extruded embedded phases do not overlap or merge with each other. Preferably the exit orifices are spaced at least 4 mm from each other.

At the same time that material 17 is forced under pressure from vane 44, upper and lower gaps 56 and 58 provide a path for first material 15 along the outside of vane 44. At point 55 in front of vane front portion 53, the two materials 15 and 17 contact each other for the first time. Material 15 from top gap 56 within die 18 forms an upper layer 61 of resulting web 12, and material 15 from bottom gap 58 of die 18 forms lower layer 63 of resulting web 12 (as shown in FIG. 4). Between these two layers 61 and 63 are discrete, discontinuous phases 59 of material 17. The combined stream of first and second material 15 and 17 continues to flow through die 18 until it leaves the die at exit port 30. The distance traveled by material 17 from leaving vane 44 until leaving die 18 at exit port 30 can be either extremely short or quite long. In fact, in certain embodiments of the invention, front portion 53 of vane 44 is positioned adjacent to exit port 30 of die 18. In other embodiments, front portion 53 of vane 44 is further removed from exit port 30, allowing a longer joint laminar flow of materials 15 and 17, as well as widening (e.g., thinning) of the phases of material 17.

FIG. 3B shows die 18 having two orifices 26 and two orifices 28. First material 15 enters die 18 at orifices 26 and then flows downstream until it is joined by second material 17, which has flowed through vane 44 after entering die 18 at orifices 28 which are connected to orifice 46. The two extrudable materials 15 and 17 flow together in substantially laminar flow through any remaining downstream portions of die 18, and subsequently exit die 18 at exit port 30 to form co-extruded web 12. Web 12 has a matrix of first material 15 formed by two layers and a plurality of discrete embedded phases 59 formed of second material 17.

The cross sections of discrete phases 59 typically do not have the exact same shape as orifices 50 in tip 53 of vane 44. This is true in certain embodiments of the invention due to the widening of the flowing stream of material 17 after it has exited vane tip 53.

The present invention is advantageous in that materials 15, 17 are co-extruded in a controlled manner. The materials are brought together in the melt state, thereby allowing for improved adhesion to one another. In addition, even when the materials are not normally compatible, they may still be co-extruded in order to produce a web retaining the properties of each of the materials. In the embodiment shown, the discrete embedded phases 59 have substantially uniform width when the orifices in vane tip 53 are substantially uniform. Although the phases 59 are often uniformly spaced across the web 12, the width, and spacing of the phases can be altered by providing different tips 53 for vane 44. The large volume of cavity 60 where the second material first enters vane 44 compared to the small volume of exit orifices 50 in the front portion 53 of vane 44 is preferred in order to obtain a pressure drop of the second material through the length of the cavity substantially less than its pressure drop through the exit orifices.

In addition, the configurations of the discrete phases may be varied by repositioning vane 44 within die 18. In particular, vane 44 may be repositioned by slight rotation in order to alter gaps 56 and 58 near vane 44 within chamber 60. In doing so, the thicknesses of the layers of the matrix in web 12 change. Gaps 56 and 58 can be changed in order to accommodate extrudable materials having differing viscosities. In embodiments where the matrix is formed of different materials to form the two layers, a different material is fed into each of the two openings 26A and B and the gaps 56 and 58 can be adjusted in order to vary the thickness of each continuous matrix layer as desired. Gaps 56 and 58 are adjusted by rotation of vane 44 such that one gap becomes larger while the other gap becomes smaller.

Vane 44 is adjusted by rotation around an axis through opening 28 having a pivotable fixture. If one matrix material is less viscous than the other, it is possible to narrow the gap through which the less viscous matrix material flows in order to maintain uniformity of the thickness of each of the two matrix layers. The gaps can be altered during processing in order to account for variations in processing conditions, such as changes in the temperature, pressure, flow rate, or viscosity over time. Thus, if die 18 has a warmer upper portion than lower portion resulting in lower viscosity of materials flowing through the upper gap, then the gaps can be adjusted to account for this change in viscosity. In addition, the gaps can be altered to achieve a different thickness in each matrix layer. This is particularly useful when each matrix layer is of a different material, e.g., a thermoplastic elastomer and a pressure-sensitive adhesive, where different properties are desired from each layer of the matrix.

Figure 2C:
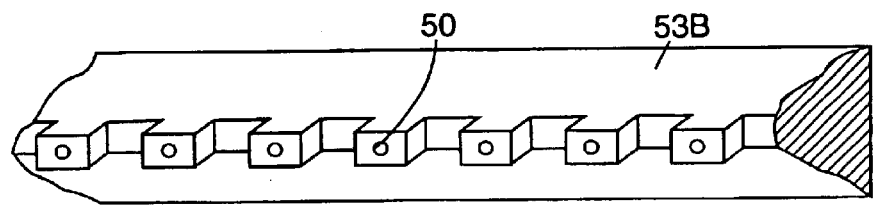
FIG. 2C is a partial perspective view of a tip of a die vane constructed in accordance with an embodiment of the invention.
Figure 5A:
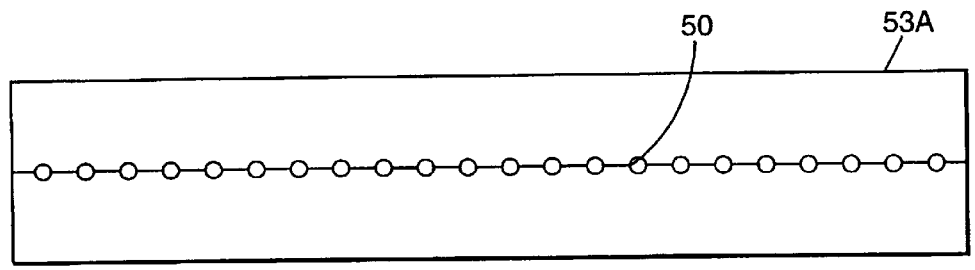
FIG. 5A is an end view of an extrusion die vane constructed in accordance with an embodiment of the invention.
Figure 5B:
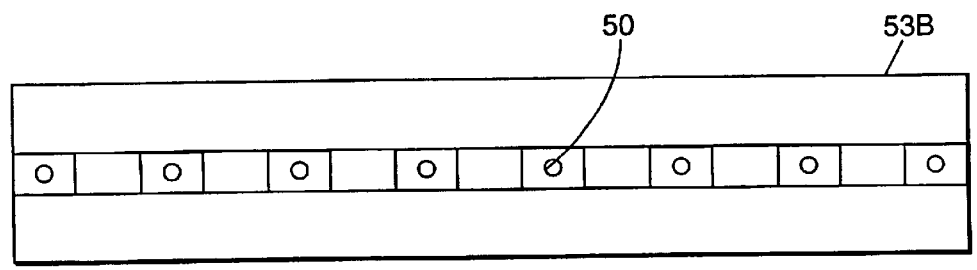
FIG. 5B is an end view of an extrusion die vane constructed in accordance with the embodiment depicted in FIG. 2C.
Figure 5C:
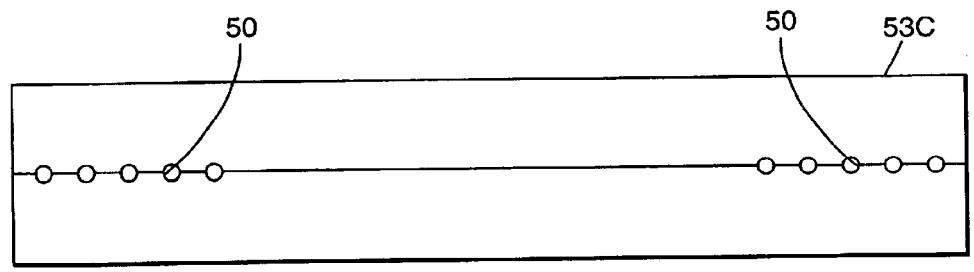
FIG. 5C is an end view of an extrusion die vane constructed in accordance with another embodiment of the invention.
Figure 5D:
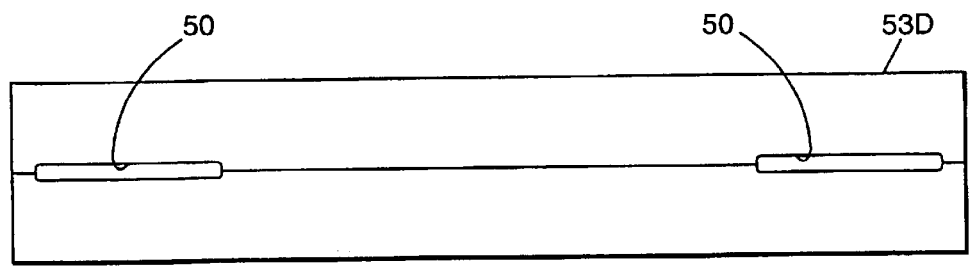
FIG. 5D is an end view of an extrusion die vane constructed in accordance with another embodiment of the invention.

In reference now to FIGS. 5A, 5B, 5C and 5D, various configurations of vane tip 53 are shown that produce different coextruded webs. In FIGS. 5A and 5B, the resultant web will have a multiplicity of discrete polymeric phases across its width. Each orifice of tip 53B is extended as shown in FIG. 2C to minimize the contact time in the die between the discontinuous phases and the layers of the continuous matrix. Tip 53C shown in FIG. 5C will yield a plurality of discrete embedded phases on each of the two edges of the extruded web, and tip 53D shown in FIG. 5D will yield one discrete embedded phase proximate each edge of the web. A web manufactured using tip 53D can be particularly suitable for cross-web stretching, since the thickened or reinforced portions on the edge of the web will provide a position onto which a stretching apparatus (e.g., tenter clips) can grab when stretching the web in a cross-web direction.

The process of the invention is able to reproduce in the embedded phases the relative dimensions of the orifices in the tip to a degree that has not previously been known. In one aspect where the orifices have substantially the same dimensions, the width of the discontinuous embedded phases are remarkably uniform. As seen in the examples in Tables 1 through 3, the coefficient of variation (COV) of the width of any three consecutive discontinuous phases is less than 8, preferably less than 5 and more preferably less than 3 percent when three or more similarly sized orifices are used. In Example 6 the same materials and process conditions were used as Example 1 and only the dimensions of the orifices in the vane tip were changed. Without any optimization of process conditions, the resulting COV for the width of any three consecutive discontinuous phases was still under 8. This compares with a COV of over 9 for the width of three consecutive phases formed with known processes and materials such as shown in Comparative Example 1. Similar width reproduction is seen even when the orifices are unevenly sized or are less than three in number. Then the uniformity becomes the consistency of measurements of the same discontinuous region but repeated over time at different down-web positions.

Another way of modifying the properties of the coextruded webs of the invention is to use specific materials having desired properties for the layers of the matrix and the embedded phases. Suitable polymeric materials for forming the matrix layers and embedded phases of the inventive coextruded web are any that can be thermally processed and include pressure sensitive adhesives, thermoplastic materials, elastomeric materials, polymer foams, high viscosity liquids, etc.

"Pressure-sensitive adhesive" means an adhesive that displays permanent and aggressive tackiness to a wide variety of substrates after applying only light pressure. It has a four-fold balance of adhesion, cohesion, stretchiness, and elasticity, and is normally tacky at use temperatures, which is typically room temperature (i.e., about 20° C. to about 30° C.). A pressure-sensitive adhesive also typically has an open time tack (i.e., period of time during which the adhesive is tacky at room temperature) on the order of days and often months or years. An accepted quantitative description of a pressure-sensitive adhesive is given by the Dahlquist criterion line (as described in *Handbook of Pressure-Sensitive Adhesive Technology*, Second Edition, D. Satas, ed., Van Nostrand Reinhold, New York, N.Y., 1989, pages 171–176), which indicates that materials having a storage modulus (G') of less than about $3 \times 10^5$ Pascal (measured at 10 radians/second at a temperature of about 20° C. to about 22° C.) have pressure-sensitive adhesive properties while materials having a G' in excess of this value do not.

"Nonpressure-sensitive adhesive" means nontacky polymeric materials, polymeric materials that are tacky when in the melt state but that do not display pressure sensitive properties, or other materials that have adhesive properties at room temperature but do not meet the Dahlquist criterion as described above. Such materials have a storage modulus (G') of at least about $3 \times 10^5$ Pascal (measured at 10 radians/second at a room temperature of about 20° C. to about 22° C.). These materials can be nontacky thermoplastic materials, which can be elastomeric or nonelastomeric. Alternatively, they can be nontacky elastomers.

Suitable materials for use in preparing the webs of the present invention, whether they are pressure-sensitive adhesives or nonpressure-sensitive adhesives, are melt processable. That is, they are fluid or pumpable at the temperatures used to melt process the webs (e.g., about 50° C. to about 300° C.), and they are film formers. Furthermore, suitable materials do not significantly degrade or gel at the temperatures employed during melt processing (e.g., extruding or compounding). Preferably, such materials have a melt viscosity of about 10 poise to about 1,000,000 poise, as measured by capillary melt rheometry at the processing temperatures and shear rates employed in extrusion.

Typically, suitable materials possess a melt viscosity within this range at a temperature of about 175° C. and a shear rate of about 100 seconds$^{-1}$.

Pressure-sensitive adhesives useful in webs of the present invention can be any material that has pressure-sensitive adhesive properties as described above at use temperatures, which are typically about room temperature (i.e., about 20° C. to about 30° C.). Generally, although not necessarily, particularly useful pressure-sensitive adhesives are amorphous with a glass transition temperature (Tg) of less than about 20° C.

The pressure-sensitive adhesive material can include a single pressure-sensitive adhesive, a mixture (e.g., blend) of several pressure-sensitive adhesives, or a mixture (e.g., blend) of a pressure-sensitive adhesive and a material that is a nonpressure-sensitive adhesive (e.g., a nontacky thermoplastic material, which may or may not be elastomeric), as long as the layer has pressure-sensitive adhesive properties. Examples of some pressure-sensitive adhesive blends are described in PCT Publication Nos. WO 97/23577, 97/23249, and 96/25469. Similarly, a suitable nonpressure-sensitive adhesive matrix layer can include a single material that is a nonpressure-sensitive adhesive, a mixture of several such materials, or a mixture of a material that is not a pressure-sensitive adhesive with a pressure-sensitive adhesive, as long as the layer does not have pressure-sensitive adhesive properties.

Pressure-sensitive adhesives useful in the present invention can be self-tacky or require the addition of a tackifier. Such materials include, but are not limited to, tackified natural rubbers, tackified synthetic rubbers, tackified styrene block copolymers, self-tacky or tackified acrylate or methacrylate copolymers, self-tacky or tackified poly-α-olefins, and self-tacky or tackified silicones. Examples of suitable pressure-sensitive adhesives are described in U.S. Pat. No. Re 24,906 (Ulrich), U.S. Pat. No. 4,833,179 (Young et al.), U.S. Pat. No. 5,209,971 (Babu et al.), U.S. Pat. No. 2,736,721 (Dexter), and U.S. Pat. No. 5,461,134 (Leir et al.), for example. Others are described in the *Encyclopedia of Polymer Science and Engineering*, vol. 13, Wiley-Interscience Publishers, New York, 1988, and the *Encyclopedia of Polymer Science and Technology*, vol. 1, Interscience Publishers, New York, 1964.

Useful natural rubber pressure-sensitive adhesives generally contain masticated natural rubber, one or more tackifying resins, and one or more antioxidants. Useful synthetic rubber adhesives are generally rubbery elastomers, which are either inherently tacky or nontacky and require tackifiers. Inherently tacky (i.e., self-tacky) synthetic rubber pressure-sensitive adhesives include for example, butyl rubber, a copolymer of isobutylene with less than 3 percent isoprene, polyisobutylene, a homopolymer of isoprene, polybutadiene, or styrene/butadiene rubber.

Styrene block copolymer pressure-sensitive adhesives generally comprise elastomers of the A-B or A-B-A type, wherein, in this context, A represents a thermoplastic polystyrene block and B represents a rubbery block of polyisoprene, polybutadiene, or poly(ethylene/butylene), and tackifying resins. Examples of the various block copolymers useful in block copolymer pressure-sensitive adhesives include linear, radial, star, and tapered block copolymers. Specific examples include copolymers such as those available under the trade designations Kraton from Shell Chemical Co., Houston, Tex., and Europrene Sol from EniChem Elastomers Americas, Inc., Houston, Tex. Examples of tackifying resins for use with such styrene block copolymers include aliphatic olefin-derived resins, rosin esters, hydrogenated hydrocarbons, polyterpenes, terpene phenolic resins derived from petroleum or terpentine sources, polyaromatics, coumarone-indene resins, and other resins derived from coal tar or petroleum and having softening points above about 85° C.

(Meth)acrylate (i.e., acrylate and methacrylate or "acrylic") pressure-sensitive adhesives generally have a glass transition temperature of about −20° C. or less and typically include an alkyl ester component such as, for example, isooctyl acrylate, 2-ethyl-hexyl acrylate, and n-butyl acrylate, and a polar component such as, for example, acrylic acid, methacrylic acid, ethylene vinyl acetate, and N-vinyl pyrrolidone. Preferably, acrylic pressure-sensitive adhesives comprise about 80 wt-% to about 100 wt-% isooctyl acrylate and up to about 20 wt-% acrylic acid. The acrylic pressure-sensitive adhesives may be inherently tacky or tackified using a tackifier such as a rosin ester, an aliphatic resin, or a terpene resin.

Poly-α-olefin pressure-sensitive adhesives, also called poly(1-alkene) pressure-sensitive adhesives, generally comprise either a substantially uncrosslinked polymer or an uncrosslinked polymer that may have radiation activatable functional groups grafted thereon as described in U.S. Pat. No. 5,209,971 (Babu et al.). Useful poly-α-olefin polymers include, for example, $C_3$–$C_{18}$ poly(1-alkene) polymers. The poly-α-olefin polymer may be inherently tacky and/or include one or more tackifying materials such as resins derived by polymerization of $C_5$–$C_9$ unsaturated hydrocarbon monomers, polyterpenes, synthetic polyterpenes, and the like.

Silicone pressure-sensitive adhesives comprise two major components, a polymer or gum and a tackifying resin. The polymer is typically a high molecular weight polydimethylsiloxane or polydimethyldiphenylsiloxane, that contains residual silanol functionality (SiOH) on the ends of the polymer chain, or a block copolymer comprising polydiorganosiloxane soft segments and urea terminated hard segments. The tackifying resin is generally a three-dimensional silicate structure that is endcapped with trimethylsiloxy groups ($OSiMe_3$) and also contains some residual silanol functionality. Silicone pressure-sensitive adhesives are described in U.S. Pat. No. 2,736,721 (Dexter). Silicone urea block copolymer pressure-sensitive adhesive are described in U.S. Pat. No. 5,461,134 (Leir et al.), PCT Publication Nos. WO 96/34028 and 96/35458.

Nonpressure-sensitive adhesive polymeric materials used in the webs of the present invention include one or more thermoplastic materials, which may or may not be elastomeric materials, and elastomers. These may be adhesive (i.e., tacky) when in the melt state or nonadhesive (i.e., nontacky) materials, as long as the adhesive materials are not pressure sensitive, as defined above.

Thermoplastic materials are generally materials that flow when heated sufficiently above their glass transition temperature and become solid when cooled. They may be elastomeric or nonelastomeric. Thermoplastic materials useful in the present invention that are generally considered nonelastomeric include, for example, polyolefins such as isotactic polypropylene, low density polyethylene, linear low density polyethylene, very low density polyethylene, medium density polyethylene, high density polyethylene, polybutylene, nonelastomeric polyolefin copolymers or terpolymers such as ethylene/propylene copolymer and blends thereof; ethylene-vinyl acetate copolymers such as those available under the trade designation Elvax from E.I. DuPont de Nemours, Inc., Wilmington, Del.; ethylene acrylic acid copolymers; ethylene methacrylic acid copolymers such as those available under the trade designation Surlyn 1702 from E.I. DuPont de Nemours, Inc.; polymethylmethacrylate; polystyrene; ethylene vinyl alcohol; polyesters including amorphous polyester; polyamides; fluorinated thermoplastics such as polyvinylidene fluoride and fluorinated ethylene/propylene copolymers; halogenated thermoplastics such as chlorinated polyethylene; polyetherblock-amides such as those available under the trade designation Pebax 5533 from Elf-Atochem North America, Inc. Philadelphia, Pa.

Thermoplastic materials that have elastomeric properties are typically called thermoplastic elastomeric materials. Thermoplastic elastomeric materials are generally defined as materials that exhibit high resilience and low creep as though they were covalently crosslinked at ambient temperatures, yet process like thermoplastic nonelastomers and flow when heated above their softening point. Thermoplastic elastomeric materials useful in the multilayer webs of the present invention include, for example, linear, radial, star, and tapered block copolymers such as those listed above with respect to pressure-sensitive adhesives (e.g., styrene-isoprene block copolymers, styrene-(ethylene-butylene) block copolymers, styrene-(ethylene-propylene) block copolymers, and styrene-butadiene block copolymers); polyetheresters such as that available under the trade designation Hytrel G3548 from E. I. DuPont de Nemours, Inc.; polyether block amides such as Pebax available from Atochem, Philadelphia, Pa.; ethylene copolymers such as ethylene vinyl acetates, ethylene/propylene copolymer elastomers or ethylene/propylene/diene terpolymer elastomers and metallocene polyolefins such as polyethylene, poly (1-hexene), copolymers of ethylene and 1-hexene, and poly(1-octene); thermoplastic elastomeric polyurethanes such as that available under the trade designation Morthane PE44–203 polyurethane from Morton International, Inc., Chicago, Ill. and the trade designation Estane 58237 polyurethane from B. F. Goodrich Company, Cleveland, Ohio; polyvinylethers; poly-α-olefin-based thermoplastic elastomeric materials such as those represented by the formula —(CH$_2$CHR)$_x$ where R is an alkyl group containing 2 to 10 carbon atoms, and poly-α-olefins based on metallocene catalysis such as Engage EG8200, ethylene/poly-α-olefin copolymer available from Dow Plastics Co., Midland, Mich.

Elastomers, as used herein, are distinct from thermoplastic elastomeric materials in that the elastomers require crosslinking via chemical reaction or irradiation to provide a crosslinked network, which imparts modulus, tensile strength, and elastic recovery. Elastomers useful in the present invention include, for example, natural rubbers such as CV-60, a controlled viscosity grade of rubber, and SMR-5, a ribbed smoked sheet rubber; butyl rubbers, such as Exxon Butyl 268 available from Exxon Chemical Co., Houston, Tex.; synthetic polyisoprenes such as Cariflex, available from Shell Oil Co., Houston, Tex., and Natsyn 2210, available from Goodyear Tire and Rubber Co., Akron, Ohio; ethylene-propylenes; polybutadienes; polybutylenes; polyisobutylenes such as Vistanex MM L-80, available from Exxon Chemical Co.; and styrene-butadiene random copolymer rubbers such as Ameripol Synpol 1011A, available from American Synpol Co., Port Neches, Tex.

Foams are those materials made by combining the above polymeric materials with blowing agents. The resulting mixtures are then subjected to various changes known in the art to activate the blowing agent used to form a multiplicity of cells within the polymer. Additional crosslinking may occur to cause resulting foams to be more stable. A particularly useful foam, when an elastic foam matrix is desired, is that disclosed in Ser. No. 09/325,963, "Breathable Polymer Foams" filed Jun. 4, 1999 and incorporated herein by reference.

High viscosity liquids are suitable as embedded phase materials. They are any liquids that do not diffuse through the matrix material and prematurely escape the article of the invention. These include, for example, various silicone oils, mineral oils and specialty materials having a sharp melting temperatures around or below room temperature.

Viscosity reducing polymers and plasticizers can also be blended with the elastomers. These viscosity reducing polymers include thermoplastic synthetic resins such as polystyrene, low molecular weight polyethylene and polypropylene polymers and copolymers, or tackifying resins such as Wingtack™ resin from Goodyear Tire & Rubber Company, Akron, Ohio. Examples of tackifiers include aliphatic or aromatic liquid tackifiers, aliphatic hydrocarbon resins, polyterpene resin tackifiers, and hydrogenated tackifying resins. Additives such as dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric phase. Suitable antistatic aids include ethoxylated amines or quaternary amines such as those described, for example, in U.S. Pat. No. 4,386,125 (Shiraki), which also describes suitable antiblocking agents, slip agents and lubricants. Softening agents, tackifiers or lubricants are described, for example, in U.S. Pat. No. 4,813,947 (Korpman) and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate.

Various additives may be incorporated into the phase(s) and/or the matrix to modify the properties of the finished web. For example, additives may be incorporated to improve the adhesion of the discontinuous phases and the matrix to one another. The co-extruded web may also be laminated to a fibrous web. Preferably, the fibrous web is a nonwoven web such as a consolidated or bonded carded web, a meltblown web, a spunbond web, or the like. The fibrous web alternatively is bonded or laminated to the coextruded web by adhesives, thermal bonding, extrusion, ultrasonic welding or the like. Preferably, the co-extruded web can be directly extruded onto one or more fibrous webs.

Short fibers or microfibers can be used to reinforce the embedded phase(s) or matrix layers for certain applications. These fibers include polymeric fibers, mineral wool, glass fibers, carbon fibers, silicate fibers and the like. Further, certain particles can be used, including carbon and pigments. Glass bubbles or foaming agents may be used to lower the density of the matrix layer or embedded phases and can be used to reduce cost by decreasing the content of an expensive material or the overall weight of a specific article. Suitable glass bubbles are described in U.S. Pat. Nos. 4,767,726 and 3,365,315. Blowing agents used to generate foams in melt processable materials are known in the art and include azodicarbonamides such as SAFOAM RIC-50 sodium bicarbonate-based chemical blowing agent. Fillers can also be used to some extent to reduce costs. Fillers, which can also function as antiblocking agents, include titanium dioxide and calcium carbonate.

A number of additional steps can optionally be performed after extrusion. For example, the web may be uniaxially or biaxially oriented, either sequentially or simultaneously, can be cured (such as through heat, electromagnetic radiation, etc.), or can be dusted with various tack-reducing agents.

The present invention is suitable for use in a number of applications. One application is an elasticized tab diaper fastener or closure. Tab diaper closures are a portion of a disposable diaper that allows the front and back of the diaper to be secured together when the diaper is placed on a child. Tab diaper closures are typically permanently secured to one half of a diaper, and include an adhesive or mechanical fastener that permits fastening of the closure to the other half of the diaper as it is placed on a child. In order to keep the diaper snugly in place on the child, it is preferable that the tab closure be elastic.

One or more discontinuous elastomeric phase(s) can be placed within a non-elastomeric matrix to form a web suitable for making an elastic diaper closure tab. The elastomeric phase is preferably 10 mm to 50 mm wide for most conventional tape tab constructions. In one embodiment of the invention, a co-extrusion die of the invention is used to form the elastic tab diaper closure. The embedded phase material is relatively elastic, such as synthetic rubber. The matrix layer material is relatively inelastic, such as polypropylene. These two materials are co-extruded using the apparatus and method of this invention such that the elastic material is substantially surrounded by the inelastic material.

Figure 6A:
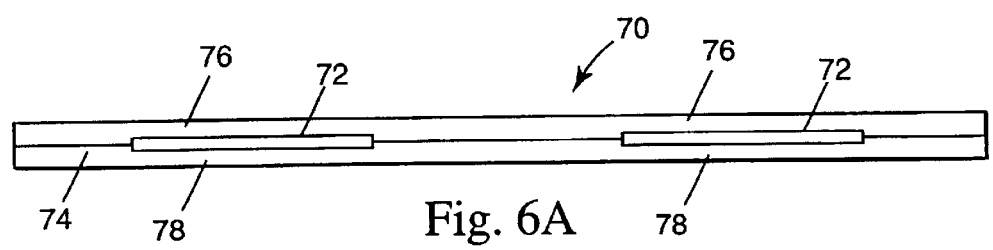
FIG. 6A is a cross-sectional view of a polymeric web made in accordance with an embodiment of the invention.

In FIG. 6A, an exemplary elastic diaper tab closure 70 is depicted. Tab closure 70 has elastic phases 72 incorporated into an inelastic polypropylene matrix 74. The elastic phases 72 are substantially surrounded by the inelastic matrix material 74. In the embodiment shown, the inelastic matrix material above and below the elastic phases is substantially thinner in the upper regions 76 and in the lower regions 78 than the elastic phases 72 to permit easy stretching of the diaper tab in the regions where the elastic phases reside. The upper and lower regions 76 and 78 may each be between 1 and 2 percent of the thickness of the elastic phases 72 in certain embodiments, and may be between 0.5 and 10 percent of the thickness of the elastic phases 72 in other embodiments. In yet other embodiments, the upper and lower regions 76 and 78 have substantially the same thickness as the elastic phase 72.

Figure 6B:
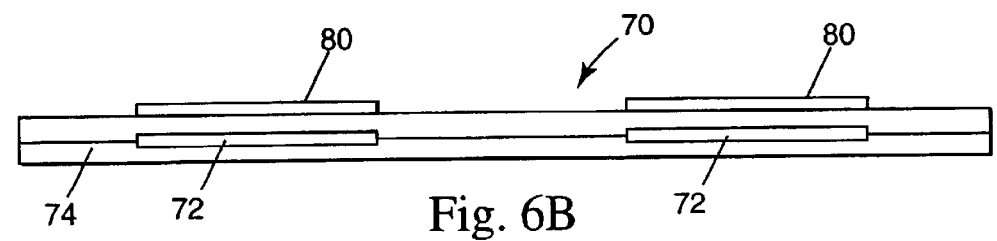
FIG. 6B is a cross-sectional view of a polymeric web made in accordance with another embodiment of the invention.
Figure 6C:
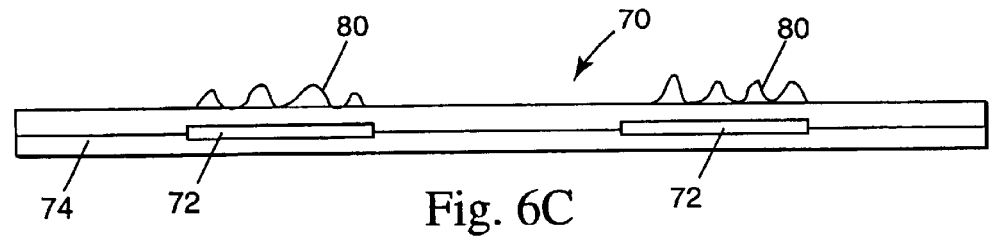
FIG. 6C is a cross-sectional view of a polymeric web made in accordance with yet another embodiment of the invention.

Referring to FIG. 6B, elastic diaper tab closures manufactured in accordance with the invention may further include an additional material, such as non-woven substrate 80 formed on one or more sides of the elastic tab closure. Co-extruded materials 72 and 74 are extruded directly onto non-woven substrates shown schematically as elongatable non-woven substrates 80, thereby achieving an intimate bond to the matrix in the elastic section. Non-woven substrate 80 may be corrugated prior to lamination to the matrix phase 76 in order to provide improved elasticity of the tab closure 70, as shown in FIG. 6C. The non-woven substrate 80 allows for cloth-like softness and handling and allows web handling in the machine direction without substantial stretch.

The fibrous web in applications similar to that mentioned above can be elastic or inelastic and extensible. When the fibrous web is inelastic and extensible, the resulting composite laminate is generally inelastic when initially stretched in a cross web direction. However, a "preactivation" step can be provided to impart or increase the elasticity of the composite laminate. The preactivation step is broadly defined as an operation performed on the fibrous web and or the composite laminate to generally weaken the strength of the fibrous web and/or inelasticly deform the fibrous web in the composite laminate in one or more directions. This allows the composite laminate to be more easily stretched while allowing reasonable recovery of the laminate to its original length when tension is removed. The prior art teaches several techniques wherein an inelastic fibrous web laminated to an elastic film is "activated". U.S. Pat. No. 5,861,074, incorporated herein by reference, discloses several ways to stretch a laminate in both the machine and cross directions to impart or improve elasticity. U.S. Pat. No. 5,143,679, incorporated herein by reference, describes a method and apparatus for incrementally stretching "zero strain" stretch laminate webs to impart elasticity thereto in the direction of initial stretching. Alternatively, U.S. Pat. No. 5,804,021, incorporated herein by reference, teaches that slits can be provided in the fibrous web to improve elasticity in one or more directions of the composite laminate eliminating the need for "activation".

In certain embodiments of the invention, the elastic tab closure is perforated in order to achieve breathability of the material. The perforations are formed, for example, by use of means to form holes through the web such as sonic, hot needle, scoring, and pin rolls.

Figure 7A:
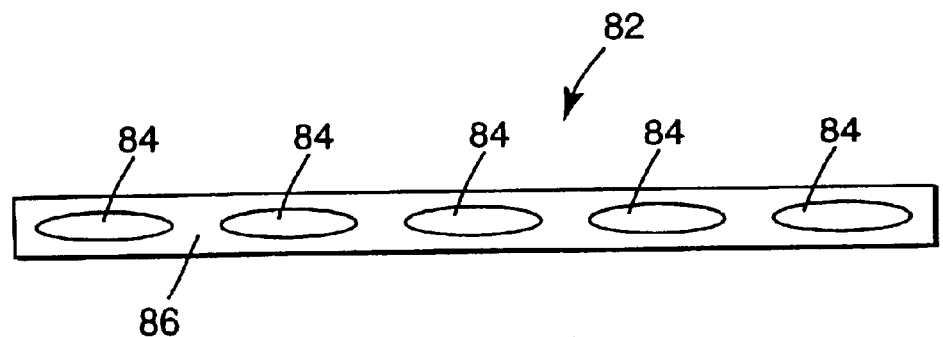
FIG. 7A is a cross-sectional view of a polymeric web constructed in accordance with an embodiment of the invention.

In yet another application of the invention, the method and apparatus are used to create a web having excellent tear resistance in the cross web direction. As depicted in FIG. 7A, the web 82 has a plurality of discrete embedded phases 84 spaced apart from each other in the cross-web direction. Discrete phases 84 are preferably resistant to tearing (i.e., they reinforce the web). The discrete phases 84 are surrounded by a continuous matrix 86. Discrete phases 84 are, for example, ultra-low density polyethylene. Matrix 86 is, for example, polypropylene. The continuous nature of the matrix allows the incorporation of phases made of a material that has little affinity for the matrix material. The phases are not able to delaminate from the matrix because they are encapsulated within the matrix. As such, these encapsulated phases avoid problems associated with materials that are extruded onto or laminated to the matrix. For example, nylon phases may be incorporated into a polypropylene matrix, even though nylon would not readily be extruded onto or laminated to a polypropylene substrate without delamination.

The web 82 is optionally stretched or oriented (in the machine direction, transverse direction, or both) in order to improve its tensile strength. For example, the web 82 may be stretched in the machine direction from about 2 to over 8 times its original extruded length. The resulting web is suitable for use as a tear-resistant tape such as a strapping tape or a carry handle; or a tear-control tape to guide a tear along the surface of a pair of discontinuous phases.

Discrete phases 84 provide improved tear resistance. As a tear propagates across the web in a cross web direction, the shear forces are distributed across a larger area when the tear meets an interface formed by two materials poorly attached to each other. Web 82 is nearly flat, and therefore has properties suitable for subsequent application of a release material and/or adhesives. In addition, web 82 can be relatively easily recycled, because in certain embodiments it is composed entirely of polymeric materials. In contrast, certain prior art materials are not readily recyclable because they contain incompatible materials, such as glass fibers, that provide the cross-web tear resistance.

Figure 7B:
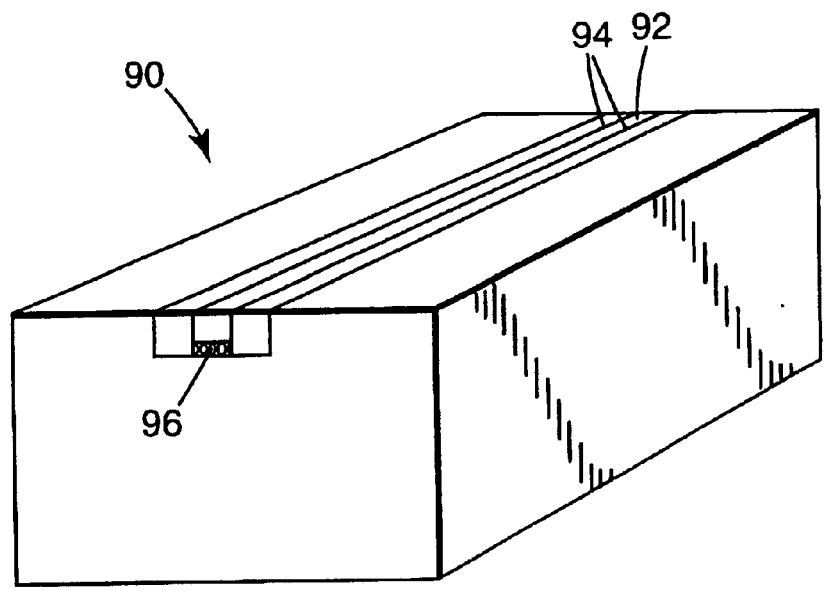
FIG. 7B is a perspective view of a box closed with a sealing web or tape made in accordance with an embodiment of the invention.

Embodiments of the invention having this improved cross-web tear resistance are suitable for use as the closure for an easy-opening box. FIG. 7B shows a box 90 sealed with a web 92 (in the form of a tape) containing at least two embedded phases 94. The phases 94 are formed by the inventive process as substantially continuous discrete embedded phases in a down-web direction within the web 92. The web 92 includes a finger lift that provides a tab 96 for lifting the end of the center portion of web 92. As the tab 96 is lifted, because of the weakness of the bond between phases 94 and the matrix polymer, the web ruptures and the tear can propagate along the embedded phases 94, thereby opening box 90. The center of the web is lifted from the box 90, leaving behind the two edges of web 92. The remaining edges can possess a rough surface that allows the easy tearing of the remaining tape in the cross-web direction to facilitate opening of the box.

An alternative tape embodiment provides placing one or more embedded phases near the surface of the web. In this embodiment, the web can be ruptured by first pulling out an embedded phase, such as by grabbing a phase end and removing the phase from the tape web, leaving behind a thin band of the web where the phase has been removed. This thin band is subsequently easily ruptured by, for example, snapping with a finger. This embodiment of the invention is suitable for use in securely sealing an envelope with an easy opening feature that also indicates tampering. Alternatively, one or more of the phases can be extruded from a polymer compound that includes a viscous liquid, such as silicone oil that preferably contains a pigment or dye. The phases are preferably sealed at various increments in the downweb direction, such as by heat sealing or crimping, thereby preventing accidental leakage of the liquid. Upon cutting or tearing of the web, the viscous liquid bleeds or exudes from the ruptured phase and provides an indication of tampering.

Co-extruded webs formed using the apparatus and method of the invention are also suitable for use in various medical articles, such as, wound dressings and tapes, surgical drapes, and wound closure systems. In certain embodiments, phases are formed in the web matrix in order to provide increased strength and improved handling without affecting the overall conformability, transparency or breathability of the polymeric material. Preferred web matrix materials for use in constructing such medical articles include polyethylene, polypropylene, styrene block copolymers such as, for example, Kraton™ block copolymers, polyester (e.g. made from Hytrel™ 4056 resin from Dupont, Wilmington, Del.), polyurethane, and combinations thereof. Preferred embedded phase materials for use in constructing such medical articles include polyamide, polyethylene, polypropylene, polyester, and polystyrene. In one preferred embodiment, non-breathable phases of polymeric material (e.g., Eastar™ 6763 polyester from Eastman Chemical Company, Kingsport, Tenn.) are formed in a breathable elastic web matrix (e.g., Estane™ 58237 polyurethane from B. F. Goodrich Company, Cleveland, Ohio) to increase strength and aid in the ability to handle and position the web in final sheet or tape form. This represents a significant improvement over current webs formed of a breathable polyurethane that are difficult to handle because they are too flexible and thus do not easily maintain a shape. Surprisingly, the addition of non-breathable phases to the breathable polyurethane web allows for retention of breathability (at least 300 grams/square meter/24 hours, and preferably at least 1,500 grams/square meter/24 hours by Moisture Vapor Transmission Rate—Upright Method) while increasing cohesive strength and web handling characteristics. In addition, the down-web tensile strength of the resulting webs typically is increased at least 500 percent over comparable webs not having discontinuous phases and preferably is increased at least 100 percent.

The precise extruders employed in the inventive process are not critical as any device able to convey melt streams to a die of the invention is satisfactory. However, it is understood that the design of the extruder screw will influence the capacity of the extruder to provide good polymer melt quality, temperature uniformity, and throughput. A number of useful extruders are known and include single and twin screw extruders. These extruders are available from a variety of vendors including Davis-Standard Extruders, Inc. (Pawcatuck, Conn.), Black Clawson Co. (Fulton, N.Y.), Berstorff Corp (North Carolina), Farrel Corp. (Connecticut), and Moriyama Mfg. Works, Ltd. (Osaka, Japan). Other apparatus capable of pumping organic melts may be employed instead of extruders to deliver the molten streams to the forming die of the invention. They include drum unloaders, bulk melters and gear pumps. These are available from a variety of vendors, including Graco LTI (Monterey, Calif.), Nordson (Westlake, Calif.), Industrial Machine Manufacturing (Richmond, Va.), Zenith Pumps Div., and Parker Hannifin Corp., (North Carolina).

Once the molten streams have exited the pump, they are typically transported to the die through transfer tubing and/or hoses. It is preferable to minimize the residence time in the tubing to avoid problems of, for example, melt temperature variation. This can be accomplished by a variety of techniques, including minimizing the length of the tubing. Alternatively, melt temperature variation in the tubing can be minimized by providing appropriate temperature control of the tubing, or utilizing static mixers in the tubing. Patterned tools which contact the web can provide surface texture or structure to improve the ability to tear the web in the cross web or transverse direction without affecting the overall tensile strength or other physical properties of the product.

EXAMPLES

This invention is further illustrated by the following examples, which are not intended to limit the scope of the invention. In the examples, all parts, ratios and percentages are by weight unless otherwise indicated. The following test methods were used to characterize the articles in the following examples:

Stress and Strain at Break The web was conditioned for 24 hours at 23° C. (73° F.) and 50 percent relative humidity (RH). Ten strips, each approximately 200 mm long and 25.4 mm wide, were cut from the web in the machine direction using razor blades. Each strip was placed in a dual speed tensile testing apparatus available from Instron Corporation, Canton, Mass. or MTS Systems Corporation, Sintech Division, Cary, N.C. With an initial jaw gap of 100 mm, the cross heads separated at 50 mm/min for the first 5 mm. The separation speed was then increased to 250 mm/min and maintained at that speed until the strips broke. The tensile testing apparatus then calculated the stress and the strain at break of the strip. Each reported value is the average of measurements on ten strips.

Cross Tear Resistance

Strips of film were cut in the down-web direction to a length of about 150 mm (6.0 in) and a width of 3.8 cm (1.5 in). A Plexiglas™ jig, cut in the shape of a triangle, was used to mark two lines on a sample at 40 degree angles from the down-web direction. The marks on the first side of the sample were 5.1 cm (2.0 in) apart and on the second side were 11.6 cm (4.56 in) apart. A nick was made with a razor blade on the first side about 6.3 mm long and between the marks.

The sample was placed in the jaws of a tester, an Instron™ tensile tester available from Instron Company, set with a crosshead speed of 51 cm/min (20 in/min), a jaw separation of 5.1 cm (2.0 in), chart speed of 51 cm/min (20 in/min) and a load cell maximum of 90.7 kg (200 lbs). The two reference lines aligned such that they were parallel to each jaw to cause the sample to be straight along the first side and form a natural bend along the second side. The sample was forced to tear when initial stress was applied. The force was measured in lbs/in and converted into Newtons/25 mm.

Tensile Strength and Elongation

Tensile strength and elongation in the down-web direction were determined in the following manner. A 10.2 cm long by 2.5 cm wide sample was placed between the jaws of an Instron™ Tensile Tester to expose a 5.1 cm gauge length. The crosshead and chart speeds were set at 25.4 cm/min. The jaws were drawn apart at 25.4 cm/min until the machine detected a break. Tensile strength, elongation, stress at break and strain at break were calculated by the Instron™ software.

Moisture Vapor Transmission Rate (MVTR)

Moisture vapor transmission rates of the samples were tested using either the upright method (A) or inverted method (B) as described below.

A-Upright Method: Glass bottles were filled with approximately 50 mL of water. Three test samples and three control samples were cut into 3.8 cm diameter samples using a round die cutter. The samples were placed between two foil rings which had holes cut in the centers. A rubber gasket was placed between the bottom of the foil and the glass container. A screw cap with a 3.8 cm diameter hole was attached to the glass jar enclosing the foil-sample sandwich and gasket to the glass. The samples were conditioned for four hours at 40 degrees C. at 20% humidity in a control chamber. The cap was then tightly secured to the jar and the jar was removed from the chamber and weighed on an analytical balance to the nearest 0.01 gram. The jars were returned to the chamber for at least 18 hrs. (at the conditions listed above). The bottles were then removed and weighed immediately to the 0.01 gram. Moisture vapor rates were calculated by the change in weight multiplied by the exposed area divided by the time they were exposed. Rates are reported in grams per square meter in 24 hours.

B-Inverted Method: The same procedure was followed as outlined above. However, after the samples were conditioned and weighed, they were returned to the chamber and the bottles were inverted so that the water contacted the test surface. The bottles were left undisturbed for at least 18 hrs. The bottles were then removed and weighed, and a moisture vapor transmission rate was calculated as above.

Peel Strength

Pressure-sensitive adhesive tape samples 1.25 cm wide and 15 cm long were tested for 180° peel adhesion to the surfaces of glass plates and/or smooth cast biaxially oriented polypropylene films. The samples were adhered to the test surfaces by rolling the tapes with a 2.1 Kg (4.5 lb.) roller using 4 passes. After aging at ambient temperatures (~22° C.) for approximately 1 hour, the tapes were tested using a Model 3M90 slip/peel tester, available from Imass, Inc., Accord, Mass., in 180° geometry at 30.5 cm/min (12 in/min) peel rate, unless otherwise noted.

| Materials Used | |
|---|---|
| Material | Description |
| 7C50 | Polypropylene/polyethylene impact copolymer, Melt Flow Index (MFI) at 175° C. of 8, available from Union Carbide Corporation, Danbury, Connecticut. |
| Vector ™ 4211 | Styrene-isoprene-styrene block co-polymer, MFI at 200° C. of 13, available from Dexco Polymers, Houston, Texas. |

Materials Used

| Material | Description |
| --- | --- |
| G-18 | Polystyrene, viscosity of 780 Pascal seconds at 204° C. and shear rate of 100 1/sec, from Huntsman Chemical, Chesapeake, Virginia. |
| 1015100S | Polypropylene/titanium dioxide concentrate available from Clariant Masterbatches Division of Clariant Corporation, Holden, Massachusetts. |
| Non-Woven A | Carded, polypropylene Nonwoven, available from BBA Nonwovens, Simpsonville, South Carolina.. |
| Dypro ™ 3271 | Polypropylene, MFI at 175° C. of 1.7, available from Fina Oil and Chemical Company, Dallas, Texas. |
| Vector ™ 4111 | Styrene-isoprene-styrene block co-polymer, MFI at 200° C. of 11, available from Dexco Polymers, Houston, Texas. |
| PS207 | Polystyrene, MFI at 175° C. of 15.5, from Huntsman Chemical, Chesapeake, Virginia. |
| Engage ™ 8200 | Ultra low-density polyethylene available from DuPont Dow Elastomer, Wilmington, Delaware. |
| Rilsan ™ BESNO P40 TL | Nylon 11 available from Elf Atochem North America, Philadelphia, Pennsylvania. |
| Estane ™ 58237 | Polyurethane available from B. F. Goodrich Company, Cleveland, Ohio. |
| Eastar ™ 6763 | PETG available from Eastman Chemical Company, Kingsport, Tennessee. |
| Dowlex ™ 10462N | High-density polyethylene available from Dow Chemical Company, Midland, Michigan. |
| Escorene ™ 3445 | Polypropylene, MFI at 175° C. of 35, available from Exxon Chemical Company, Polymers Group, Houston, Texas. |
| Tenite ™ 1550P | Low-density polyethylene, Melt Index (MI) of 3.5, available from Eastman Chemical Company, Kingsport, Tennessee. |
| PSA A | An acrylic pressure-sensitive adhesive (PSA) (95 weight percent isooctyl acrylate/5 weight percent acrylic acid, water emulsion polymerized, shear viscosity - 150 Pa-s), prepared according to U.S. Pat. No. RE 24,906, (Ulrich) and dried. |
| PSA B | An acrylic PSA (96 weight percent isooctyl acrylate/4 weight percent methacrylic acid, water suspension polymerized), prepared according to U.S. Pat. No. 4,833,179 (Young) which is dried to about 90 wt. percent and melt blended with Foral ™ 85 (a tackifying resin available from Hercules Inc., Wilmington, Delaware) in a wt. ratio of acrylate to Foral ™ of 80:20. |
| SAFOAM ™ Ric-50 | A sodium bicarbonate-based chemical-blowing agent available from Reedy International Corp., Keyport, New Jersey. |

Examples 1–2 and Comparative Example 1

Examples 1–2 demonstrate some effects of various process variables on constructions having inelastic matrices and elastic embedded phases.

In Example 1, an extrusion was carried out using a 45 cm (18 in) wide Cloeren™ two-layer multi-manifold die (available from Cloeren Co., Orange, Tex.) that had been modified. The vane had been hollowed out as shown in FIGS. 3A and 3B, and the leading edge or tip had been cut off to make a vane manifold. A new vane tip containing five orifices was fabricated and mounted to the vane manifold with a number of small socket head bolts. Preferably, these bolts were tightened with a torque wrench at a torque of about 11.3 Newton-meters (100 in. $lb_f$), in order to prevent leakage. Five orifices were spaced across the vane tip, each having an oblong cross-sectional shape with a width of about 15 mm (0.600 inches), a height of about 0.38 mm (0.015 inches) and a spacing between orifices of about 760 mm (3.00 inches), respectively. The length of these orifices was about 6 mm.

An inelastic matrix material, 7C50 polypropylene/polyethylene (PP/PE), was fed with an extruder (64 mm (2.5-inch) Davis-Standard™ single screw extruder available from Davis-Standard Corp., Pawcatuck, Conn.) through two inlet manifolds of the co-extrusion die. The matrix material extruder was operated at 10 rpm with a head pressure of 9.0 MPa (1300 psi) to feed matrix material at a rate of about 6.0 kg/hr (13.2 lbs/hr). An elastic phase material, a mixture of Vector™ 4211 SIS block copolymer, G-18 polystyrene and 1015100S white pigment concentrate in a weight ratio of 85:15:1 was fed with an extruder (38 mm (1.5-inch) Davis-Standard™ single screw extruder) through the modified vane in the die. The embedded phase material extruder was operated at 40 rpm with a head pressure of 3.2 MPa (470 psi) to feed elastic material at a rate of about 11.5 kg/hr (25.2 lbs/hr). Preferably, the extruder is operated to bring the flow rate of material through it gradually up to the desired rate. Both extruders were operated using a temperature profile of zone 1—163° C. (325° F.), zone 2—218° C. (425° F.), zone 3—232° C. (450° F.) and zone 4—243° C. (470° F.). The die was operated at 243° C. (470° F.). The extrudate comprising a two-layer polymer matrix containing embedded phases running down-web was extruded from the die into a nip formed by a chrome casting wheel, at 7.2° C. (45° F.) and a silicone coated nip roll, at 7.2° C. The web take-away or handling system operated at about 16.8 m/min (55 fpm).

Example 2 was made as Example 1 except the continuous matrix material extruder was run at 20 rpm with a head pressure of 12.4 MPa (1800 psi) to feed matrix material at a rate of about 11.8 kg/hr (26.0 lbs/hr).

Comparative Example 1 was made as Example 1 except a different die was used and some conditions were changed. The extrusion was carried out using a 45 cm wide Cloeren™ three-layer multi-manifold die that had been modified as described in U.S. Pat. No. 5,429,856 (Krueger), Example 1. A 'comb' insert was bolted to the internal surface of one of the two unmodified vanes and snugly engaged with the second vane to allow the vanes to rotate in unison. The 'comb' insert had five orifices cut into the metal which allowed material from the center manifold to flow into phases. The three center orifices had a width of 19 mm (0.750" in) and the two outside orifices of about 6.4 mm (0.250" in). All the slots were separated by a space of 102 mm (4.00 in).

The matrix material was extruded through both of the outer manifolds and the phase material was extruded into the middle manifold and through the comb insert. The first outer layer was fed from a first extruder (38 mm (1.5-inch) Davis-Standard™ single screw extruder). The second outer layer was fed from a second extruder (34 mm Leistritz™ fully intermeshing, co-rotating twin screw extruder available from American Leistritz Extruder Corp., Somerville, N.J.) fitted with a gear pump. The embedded phase material was extruded with a 51 mm (2.0-inch) Berlyn™ single screw extruder available from Berlyn Corp., Worchester, Mass. that was fitted with a gear pump to meter the material from the extruder. The first extruder was run at 15 rpm with a head pressure of about 9.7 MPa (1740 psi) to feed the first layer of matrix material at a rate of about 3.2 kg/hr (7.0 lbs/hr). The second extruder had a screw speed of 70 rpm, a gear pump speed of 7 rpm and a head pressure of 9.1 MPa (1320 psi) to feed the second layer of matrix material at a rate of about 3.2 kg/hr (7.0 lbs/hr). The Berlyn extruder had a screw speed of 19 rpm, a gear pump speed of 25 rpm and a head pressure of 9.5 MPa (1370 psi) to feed the embedded phase material at a rate of about 11.4 kg/hr (25.0 lbs/hr). The web take-away system ran at a speed of about 9.1 m/min (30 fpm).

The width in the cross-web direction for each example was measured for each of the five embedded phases and an average, standard deviation and coefficient of variation (COV) (standard deviation/average) in percent for the three consecutive phases from similar sized orifices but having the greatest width variation were calculated for the width dimension. Results are reported in Table 1.

TABLE 1

|  | Example 1 Width mm | Comparative Ex. 1 Width mm | Example 2 Width mm |
|---|---|---|---|
| Phase 1 | 25.40 | 7.87 | 25.40 |
| Phase 2 | 26.92 | 33.27 | 25.40 |
| Phase 3 | 26.92 | 38.10 | 25.40 |
| Phase 4 | 28.45 | 31.75 | 25.40 |
| Phase 5 | 26.92 | 7.87 | 23.81 |
| Average | 26.41 | 34.37* | 24.87 |
| Std Dev | 0.88 | 3.32* | 0.92 |
| COV (%) | 3.32 | 9.65* | 3.68 |

*Includes only phases 2–4 because those phases were formed from orifices having similar dimensions.

As seen in Table 1, the widths of the embedded phases in Examples 1 and 2 were substantially uniform, indicating that the flow-rates to those phases were substantially the same. In contrast, the widths of Comparative Example 1 varied substantially where the material came from orifices having the same dimensions, as indicated in Table 1 by the COV values, indicating that the flow-rates to those regions had substantially greater variation than Examples 1 and 2. White pigmented embedded phase material had a definite boundary and did not extend into the adjacent matrix material for Examples 1 and 2. For Comparative Example 1, white pigmented phase material did extend into the matrix material.

Examples 3–5

Examples 3–5 demonstrate changing melt viscosity of the embedded phase material on constructions having inelastic matrices and elastic embedded phases.

Example 3 was made as in Example 1 except some process conditions were changed. The matrix material extruder was run at 30 rpm with a head pressure of 15.2 MPa (2200 psi) to feed matrix material. The embedded phase material extruder was run at 80 rpm with a head pressure of 13.8 MPa (2000 psi) to feed embedded phase material. The web take-away system ran at a speed of about 16.8 m/min (40 fpm).

Examples 4 and 5 were made as in Example 3 except the material ratios of the embedded phase material were changed to alter melt viscosity. In Example 4 and 5 the weight ratios of Vector™ 4211 SIS block copolymer (having a viscosity of 780 Pascal-seconds at a shear rate of 100 $sec^{-1}$ at 204° C.), G-18 polystyrene (having a viscosity of 420 Pascal-seconds at a shear rate of 100 $sec^{-1}$ at 204° C.) and white pigment concentrate were in a weight ratio of 90:10:1 and 80:20:1, respectively.

The thickness and width in the cross-web direction for each example were measured for each of the five embedded phases and an average, standard deviation and COV for the three consecutive phases having the greatest variation were calculated for the width dimension. Results are reported in Table 2.

TABLE 2

|  | Thickness | Width | | |
|---|---|---|---|---|
| Example | Avg in mm | Avg in mm | Std Dev in mm | COV in % |
| 3 | 0.19 | 34.40 | 0.92 | 2.66 |
| 4 | 0.18 | 38.63 | 0.92 | 2.37 |
| 5 | 0.20 | 34.40 | 0.92 | 2.66 |

As seen above, the phases became narrower as the viscosity of the elastomeric blend was reduced and wider as the viscosity was increased.

Examples 6–7

Examples 6–7 demonstrate the effect of vane tip design and selection of extrudable materials on constructions having inelastic matrices and elastic embedded phases.

Example 6 was made as in Example 1 except the polystyrene was changed, the vane tip configuration was different and some process conditions were changed. PS207 polystyrene was used in place of G-18 polystyrene. The exit orifices in the vane were 50% wider in cross-section (22.8 mm (0.900 in)) and four were used instead of five. The matrix material extruder was run at 15 rpm with a head pressure of 10.4 MPa (1500 psi) to feed matrix material, and the embedded phase material extruder was run at 40 rpm with a head pressure of 3.2 MPa (470 psi) to feed embedded phase material to the die. The web take-away system ran at a speed of about 15.2 m/min (50 fpm).

Example 7 was made as Example 6 except the materials were different and some process conditions were changed. The matrix material was 7C50 polypropylene/polyethylene copolymer and the embedded phase material was Vector™ 4111 SIS block copolymer, PS207 polystyrene (a pre-blended mixture) and white pigment concentrate in a weight ratio of 85:15:1. The matrix material extruder was run at 15 rpm with a head pressure of 10.4 MPa (1500 psi) to feed matrix material, and the embedded phase material extruder was run at 50 rpm with a head pressure of 3.7 MPa (540 psi) to feed SIS/polystyrene/pigment blend. The web take-away system ran at a speed of about 14.6 m/min (48 fpm).

The width in the cross-web direction for each example were measured for each of the four phases and an average, standard deviation and COV for the three consecutive phases having the greatest variation in percent were calculated for the width dimension. Results are reported in Table 3.

TABLE 3

|  | Example 6 Width mm | Example 7 Width mm |
|---|---|---|
| Phase 1 | 33.34 | 57.15 |
| Phase 2 | 38.10 | 58.74 |
| Phase 3 | 38.10 | 57.15 |
| Phase 4 | 33.34 | 55.56 |
| Average | 36.51 | 57.15 |
| Std Dev | 2.75 | 1.59 |
| COV (%) | 7.5 | 2.8 |

As seen, the width of the phases and the COV values were influenced by both the materials and the vane tip configuration.

Example 8

Example 8 demonstrates that other webs can be laminated onto constructions of the invention. Example 8 was made as in Example 1 except the matrix extruder speed was 15 rpm, the take-away speed was 10.7 m/min (35 fpm) and two non-woven webs were laminated to the web construction. Two webs of Non-Woven A were fed into the nip to produce a construction having elastic phases uniformly spaced in an inelastic matrix covered by non-woven material.

Examples 9–11

Examples 9–11 demonstrate some effects of having matrix materials and embedded phase materials that were different or similar where the matrix materials were inelastic and the phases were either elastic or inelastic.

Example 9 was made as in Example 1 except the vane tip configuration and materials were different, some process conditions were changed and some were added. The vane tip had circular exit orifices each having a diameter of 508 microns (20 mils) and separated by a space of 4.1 mm (0.160 in) and extended from the vane tip 2.5 mm (0.100 in) into the matrix flow as shown in FIG. 2C. The length of these orifices was about 5 mm. The matrix material was an inelastic thermoplastic, Dypro™ 3271 polypropylene and the embedded phase material was Engage™ 8200 polyethylene. The temperature profiles in both extruders were: zone 1—191° C. (375° F.), zone 2—232° C. (450° F.), zone 3—271° C. (520° F.) and zone 4—271° C. (520° F.). The die was operated at 271° C. (520° F.). The matrix material extruder was run at 75 rpm with a head pressure of 26.9 MPa (3900 psi) to feed matrix material. The embedded phase material extruder was run at 41 rpm with a head pressure of 19.3 MPa (2800 psi) to feed embedded phase material. The web take-away system ran at a speed of about 3.7 m/min (12 fpm) resulting in a total web thickness of 533 microns (21 mils). The resulting web was then stretched 6:1 in the down-web direction. The orientation temperature was 115° C. (240° F.).

Example 10 was made in a manner similar to Example 9 except the embedded phase material was different and some conditions were changed. The embedded phase material was an inelastic thermoplastic, Rilsan™ BESNO P40 TL nylon. The stretch ratio was 5:1.

Example 11 was made in a manner similar to Example 9 except the embedded phase material was the same as the matrix material, stretch ratio was 7:1, and some equipment and conditions were changed. The matrix material was fed with an 88 mm (3.5-inch) Davis-Standard™ single screw extruder that was operated with a temperature profile of zone 1—199° C. (390° F.), zone 2—216° C. (420° F.) and zones 3 to 6—238° C. (460° F.). The 88 mm extruder was run at 16.2 rpm with a head pressure of 22.9 MPa (3320 psi) to feed matrix material. The embedded phase material was fed with a 51 mm (2.0-inch) Davis-Standard™ single screw extruder that was operated with a temperature profile of zone 1—182° C. (360° F.), zone 2—191° C. (375° F.) and zones 3 to 5—271° C. (460° F.). The 51 mm extruder was run at 17.4 rpm with a head pressure of 19.0 MPa (2750 psi) to feed embedded phase material. The die was operated at 260° C. (500° F.). The orientation temperature was 127° C. (260° F.).

Comparative Example 2 was tensilized polypropylene film (stretch ratio approximately 7:1, thickness 84 microns) available as V/N 98105/06-1d from Nowofol, Siegsdorf, Germany.

Examples 9–11 and Comparative Example 2 were tested for Stress and Strain at Break and Cross Tear Resistance. Results are reported in Table 4.

TABLE 4

| Example | Stress at Break MPa (kpsi) | Strain at Break % | Cross Tear Resistance N/25 mm (lb/in) |
|---|---|---|---|
| 9 | 255 (37) | 29 | 128 (28.75) |
| 10 | 283 (41) | 33 | 237 (53.25) |
| 11 | 414 (60) | 34 | 5.5 (1.25) |
| C-2 | 333 (48) | 36 | 3.3 (0.75) |

Figure 8:
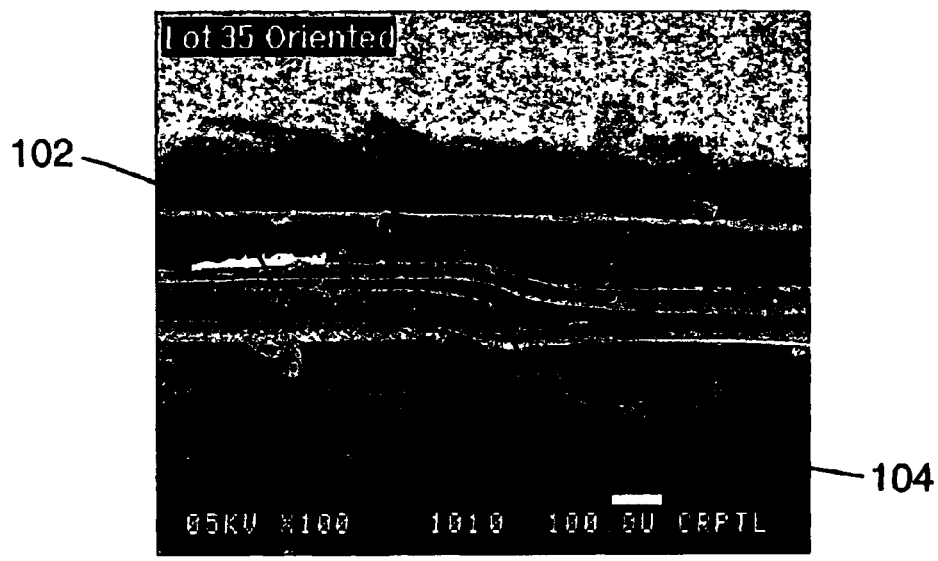
FIG. 8 is a photo-micrograph of a cross section of a polymeric web made in accordance with an embodiment of the invention shown in Example 10.

As seen in Table 4, the presence of the different inelastic thermoplastic embedded phases in Examples 9 and 10 reduced the stress at break of the web, but also significantly increased the cross tear resistance of the web. FIG. 8 shows a cross-section of Example 10. The embedded phase material 102 is shown to have delaminated from the matrix material by the space 104 between the embedded phase 102 and the matrix. A knit line between the two matrix material layers was still visible even though the layers were made of the same materials.

In addition, when the phases are of the same material as the matrix, the stress at break for tensilized web is significantly higher than tensilized web made without phases. The film of Example 11 was observed under a microscope using cross-polarizing filters, and bands were observed in the film. When it was slit, strands of the embedded phase polymer could be seen and separated from the film, indicating that; although the same polymer had been used for both phases, the matrix polymer and the polymer leaving the vane did not fuse together into a single phase.

Examples 12–13 and Comparative Example 3

Examples 12–13 demonstrate characteristics of a web having elastic matrices and inelastic phases.

Example 12 was made as Example 9 except the matrix material and embedded phase material were different and some equipment and conditions were changed. The matrix material was an elastic material, Estane™ 58237 polyurethane. It was fed with a 51 mm (2.0-inch) Berlyn™ single screw extruder that was operated at a temperature profile of zone 1—149° C. (300° F.), zone 2—171° C. (340° F.) and zones 3—7–204° C. (400° F.). The 51 mm extruder was run at 25 rpm with a head pressure of 31.1 MPa (4500 psi) to feed matrix material. The embedded phase material was an inelastic thermoplastic polymer, Eastar™ 6763 glycol modified polyester. It was fed with an 32 mm (1.25-inch) Killion™ single screw extruder (available from Davis-Standard Killion Systems, Cedar Grove, N.J.) that was operated with a temperature profile of zone 1—188° C. (370° F.), zone 2—227° C. (440° F.) and zones 3 and 4—243° C. (470° F.). The 32 mm extruder was run at 6 rpm with a head pressure of 15.9 MPa (2300 psi) to feed phase material. The die was operated at 218° C. (425° F.). The web take-away speed was 11.3 m/min (37 fpm) resulting in an overall matrix thickness of approximately 50 microns (2.0 mils). The cast web was not oriented.

Example 13 was made as Example 12 except the embedded phase material was different and some conditions were changed. The temperature profile for the extruder that fed the matrix material was zone 1—149° C. (300° F.), zone 2—166° C. (330° F.) and zones 3 to 7—199° C. (390° F.). The 51 mm was run at 10 rpm with a head pressure of 13.8 MPa (2000 psi) to feed matrix material. The embedded phase material was an inelastic thermoplastic polymer, Dowlex™ 10462N polyethylene. The temperature profile of the 32 mm extruder that fed this material was zone 1—182° C. (360° F.), zone 2—241° C. (465° F.) and zones 3 and 4—249° C. (480° F.). The 32 mm extruder was operated at 12 rpm with a head pressure of 3.5 MPa (500 psi) to feed phase material. The temperature of the nip rolls was approximately 16° C. (60° F.). The web take-away speed was 5.2 m/min (17 fpm) resulting in an overall matrix thickness of approximately 50 microns (2.0 mils).

Comparative Example 3 was made by extruding the polyurethane matrix material of Example 12 by conventional extrusion methods into a web having a thickness of approximately 50 microns (2.0 mils).

Examples 12–13 and Comparative Example 3 were tested for Tensile Strength and Elongation and MVTR. Results are reported in Table 5.

TABLE 5

| Example | Tensile Strength MPa (lbs/in$^2$) | Elongation percent | MVTR g/m$^2$/24 hrs | |
|---|---|---|---|---|
| | | | A | B |
| 12 | 38.6 (5600) | 515 | 8900 | NA |
| 13 | 37.6 (5451) | 498 | NA | 1446 |
| C-3 | 11.4 (1650) | 545 | 7200 | 1800 |

Figure 9:
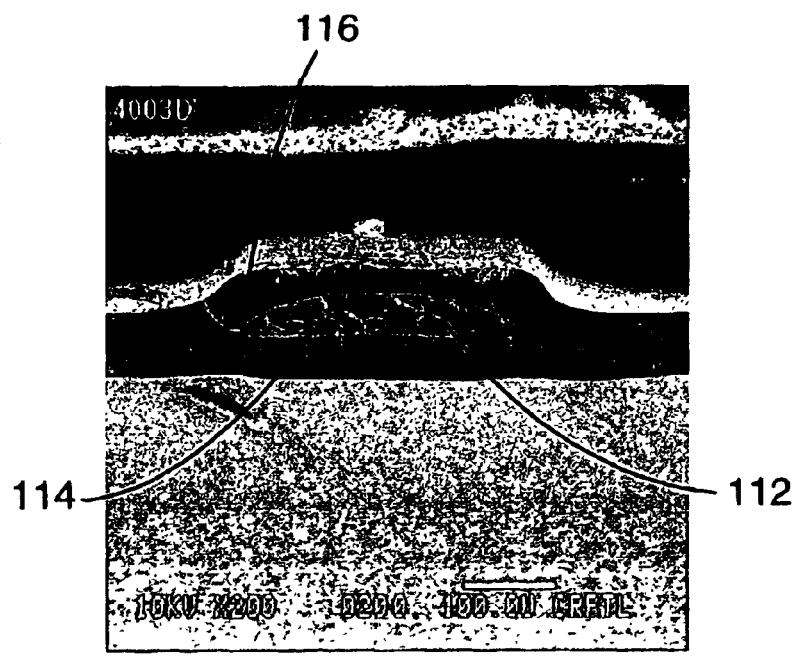
FIG. 9 is a photo-micrograph of a cross section of a polymeric web made in accordance with an embodiment of the invention shown in Example 13.

As seen, the presence of embedded phases of inelastic thermoplastic material significantly increased the tensile strength of the overall construction without reducing its moisture vapor transmission rate. FIG. 9 shows knit lines from the web of Example 13. The embedded phase material 112 is embedded between the lower layer 114 and upper layer 116 of matrix material. The two matrix layers 114 and 116 are joined such that a knit line between the two matrix layers was still visible even though the layers were made of the same materials.

Example 14

Example 14 demonstrates a construction in which the two layers of matrix material are different.

Example 14 was made in a manner similar to Example 12 except the two layers of matrix material were made of different materials and an additional extruder (equipped with a gear pump to convey extrudate to the die) was used. The first layer of matrix material was made of a tacky elastomeric material, PSA B, and the second layer was made of the elastic thermoplastic polymer, Estane™ 58237 polyurethane. The first matrix material was fed with a first extruder, a 34 mm fully intermeshing, co-rotating Leistritz™ twin screw extruder that used an increasing temperature profile reaching a peak temperature of 193° C. (380° F.). The 34 mm extruder was run at 180 rpm with gear pump speed of 4.7 rpm and a head pressure of 4.2 MPa (610 psi) to feed one matrix material into the first matrix feed orifice 26A of the die. The second matrix material was fed with the 51 mm extruder into the second matrix feed orifice 26B of the die.

The resulting construction, which comprised a web having a PSA on one side, a polyurethane on the opposite side, and polyester embedded strands, provides an example of a matrix composed of two different materials.

Examples 15–16 and Comparative Example 4

Examples 15–16 demonstrate some effects of having tacky matrices and elastic phases.

Example 15 was made in a manner similar to Example 12 except the matrix and embedded phase materials were different and the process conditions were changed. The matrix material was made of a tacky PSA A, and the embedded phase material was made of the thermoplastic polymer, Escorene™ 3445 polystyrene. The temperature profile for the extruder that fed the matrix material was zone 1—121° C. (250° F.), zone 2—149° C. (300° F.), zone 3—182° C. (360° F.), zone 4—204° C. (400° F.) and zones 5 to 7—210° C. (410° F.). The 51 mm matrix polymer extruder was run at 31 rpm, and it was equipped with a gear pump to convey extrudate to the die, said pump running at a speed of 15 rpm and a head pressure of 10.4 MPa (1500 psi) to feed matrix material. The temperature profile of the embedded phase material extruder was zone 1—121° C. (250° F.), zone 2—193° C. (380° F.) and zones 3 and 4—210° C. (410° F.). The 32 mm embedded phase extruder was run at 5 rpm with a head pressure of 3.4 MPa (490 psi) to feed embedded phase material. The die temperature was 210° C. (410° F.) and the nip temperature was approximately 21° C. (70° F.).

Example 16 was made as in Example 15 except some process conditions were changed. The 32 mm extruder was run at 10 rpm with a head pressure of 4.5 MPa (650 psi) to feed embedded phase material.

Comparative Example 4 was made as in Example 15 except no embedded phase material was present and the 32 mm diameter extruder was not used.

Examples 15–16 and Comparative Example 4 were tested for Tensile Stress at Break and Strain at Break, using the Tensile Strength and Elongation test, and Peel Adhesion to Glass. Results are reported in Table 6. TABLE 6

TABLE 6

| Example | Tensile Stress at Break MPa (psi) | Strain at Break percent | Peel Adhesion g/dL (oz/in) |
|---|---|---|---|
| 15 | 4.5 (656) | 858 | 25.2 (23) |
| 16 | 6.2 (892) | 875 | 20.8 (19) |
| C-4 | 0.5 (75) | 743 | 26.3 (24) |

As seen, the presence of the embedded inelastic phases resulted in substantially increased tensile stress and strain at break without a great deal of loss in peel adhesion to glass.

Example 17 and Comparative Example 5

Example 17 demonstrates the characteristics of a web having inelastic phases in foamed matrices.

Example 17 was made in a manner similar to Example 12 except the matrix and embedded phase materials were different and the process conditions were changed. The matrix material was made of a pre-blended mixture of inelastic thermoplastic polymer, Tenite™ 1550P polyethylene, and chemical blowing agent, SAFOAM™ Ric-50, in a weight ratio of 100:2 and the embedded phase material was Tenite™ polyethylene alone. The 51 mm extruder was equipped with a gear pump to convey extrudate to the die. The temperature profile for the extruder that fed the matrix material was zone 1—121° C. (250° F.), zone 2—149° C. (300° F.), zone 3—182° C. (360°F.), zone 4—182° C. (360° F.), zone 5— 221° C. (430° F.) and zones 6 and 7—188° C. (370° F.). The 51 mm extruder was operated at 13 rpm with a gear pump speed of 15 rpm and a head pressure of 10.4 MPa (1500 psi) to feed matrix material. The temperature profile of the embedded phase material extruder was zone 1–149° C. (300° F.), zone 2–204° C. (400° F.) and zones 3 and 4–216° C. (420° F.). The 32 mm extruder was run at 15 rpm with a head pressure of 13.8 MPa (2000 psi) to feed embedded phase material. The die temperature was 199° C. (390° F.) and the nip temperature was approximately 21° C. (70° F.).

Comparative Example 5 represents a portion of Example 17 where there were no phases embedded within the foamed matrix material.

Example 17 and Comparative Example 5 were tested for Stress and Strain at Break. Results are reported in Table 7.

TABLE 7

| Example | Stress at Break MPa (psi) | Strain at Break percent |
|---|---|---|
| 17 | 3.35 (485) | 150 |
| C-5 | 1.62 (235) | 83 |

As seen, the presence of inelastic embedded phases within the foam matrix resulted in a tougher and more durable web construction.

We claim:

1. A process for making a polymeric co-extruded web, the process comprising:

a) providing at least one extrudable matrix material and a second extrudable material;

b) providing a die containing two chambers, each having an upstream and downstream end, and a vane positioned between the two chambers forming a wall of each chamber so that there are at least two gaps between the outside of the vane and the inside of the chambers through which polymer can flow, the vane containing a cavity having at least one input orifice positioned to receive extrudable material and a plurality of exit orifices oriented to extrude polymer toward the downstream end of the chamber; and c) extruding the extrudable matrix material through the two chambers of the die and the second extrudable material through the input and exit orifices in the vane to produce a co-extruded web comprising a continuous matrix comprising the matrix material, and said second extrudable material which is contained within the matrix as a separate phase wherein the number and size of exit orifices in the vane and the cross section of the cavity normal to the direction in which extrudable material flows into it are sufficient to yield a ratio of the pressure drop through the exit orifices $\Delta P_{orifice}$ to pressure drop through the cavity $\Delta P_{cavity}$ of at least about 1.5 calculated using the flow rate equation for a power-law fluid, assuming the same flow rate through all exit orifices of the same cross section.

2. The process for making a polymeric co-extruded web according to claim 1, further comprising orienting the web in at least one direction.

3. The process for making a polymeric co-extruded web according to claim 2, wherein two different matrix materials are used, one matrix material is extruded through one chamber of the die and the other matrix material is extruded through the other chamber.

4. An extrusion die for forming a polymeric co-extruded web, the die comprising:
 a body containing at least two chambers each having an upstream end and a downstream end; and
 at least one vane positioned between the chambers of the body to form a wall of each chamber so that the length dimension of the vane is approximately transverse to the direction polymer is intended to flow through the die chambers, said vane having a cavity having a front portion oriented toward the downstream end of the die, at least one input orifice positioned to convey extrudable material into the cavity, and a plurality of exit orifices positioned in the front portion of the vane to extrude material toward the downstream end of the die body wherein the number and size of exit orifices in the vane and the cross section of the cavity normal to the direction in which extrudable material flows into it are sufficient to yield a ratio of the pressure drop through the exit orifices $\Delta P_{orifice}$ to pressure drop through the cavity $\Delta P_{cavity}$ of at least about 1.5 calculated using the flow rate equation for a power-law fluid, assuming the same flow rate through all exit orifices of the same cross section.

5. The extrusion die according to claim 4, wherein the vane further comprises a removable tip along the end facing the downstream portion of the die and the vane is pivotable about an axis passing through the upstream portion of the vane.

* * * * *